US012753446B2

(12) United States Patent
Rodriguez et al.

(10) Patent No.: US 12,753,446 B2
(45) Date of Patent: Oct. 6, 2026

(54) USE OF SIMULTANEOUS MARKER DETECTION FOR ASSESSING DIFFUSE GLIOMA AND RESPONSIVENESS TO TREATMENT

(71) Applicant: BioVentures, LLC, Little Rock, AR (US)

(72) Inventors: Analiz Rodriguez, Little Rock, AR (US); Thidathip Wongsurawat, Little Rock, AR (US)

(73) Assignee: BioVentures, LLC

( * ) Notice: Subject to any disclaimer, the term of this patent is extended or adjusted under 35 U.S.C. 154(b) by 1048 days.

(21) Appl. No.: 17/767,784

(22) PCT Filed: Oct. 12, 2020

(86) PCT No.: PCT/US2020/055256
§ 371 (c)(1),
(2) Date: Apr. 8, 2022

(87) PCT Pub. No.: WO2021/072374
PCT Pub. Date: Apr. 15, 2021

(65) Prior Publication Data

US 2024/0084389 A1 Mar. 14, 2024

Related U.S. Application Data

(60) Provisional application No. 62/914,141, filed on Oct. 11, 2019.

(51) Int. Cl.
*C12Q 1/6886* (2018.01)
*C12Q 1/6869* (2018.01)

(52) U.S. Cl.
CPC ......... *C12Q 1/6886* (2013.01); *C12Q 1/6869* (2013.01); *C12Q 2600/106* (2013.01); *C12Q 2600/154* (2013.01); *C12Q 2600/156* (2013.01)

(58) Field of Classification Search
CPC ................ C12Q 1/6886; C12Q 1/6869; C12Q 2600/106; C12Q 2600/154; C12Q 2600/156; C12Q 2521/525; C12Q 2525/191; C12Q 2535/122; C12Q 2537/164; G01N 33/57407; G01N 2800/52; C12N 9/22
See application file for complete search history.

(56) References Cited

U.S. PATENT DOCUMENTS

2018/0330049 A1 11/2018 Iavarone et al.

FOREIGN PATENT DOCUMENTS

CN 106995850 A 8/2017
CN 110129441 A 8/2019
CN 110211633 A 9/2019

OTHER PUBLICATIONS

Yan, IDH1 and IDH2 Mutations in Gliomas, The New England Journal of Medicine, Feb. 2009, 360, 765-773 (Year: 2009).*
Mikeska, Optimization of Quantitative MGMT Promoter Methylation Analysis Using Pyrosequencing and Combined Bisulfite Restriction Analysis, The Journal of Molecular Diagnostics, Jul. 2007, 9, 368-381 (Year: 2007).*
Gilpatrick, Targeted Nanopore Sequencing with Cas9 for studies of methylation, structural variants, and mutations, Jun. 2019, 1-12 , biorxiv.com [retrieved on May 1, 2025]. Retrieved from the Internet: <URL: https://www.biorxiv.org/content/10.1101/604173v2.full> (Year: 2019).*
GenBank accession No. NG_052673.1 [online]. GenBank, [2017] [retrieved on May 1, 2025]. Retrieved from: https://www.ncbi.nlm.nih.gov/nuccore/NG_052673.1 (Year: 2017).*
GenBank accession No. NG_023319.2 [online]. GenBank, [2018] [retrieved on May 1, 2025]. Retrieved from: https://www.ncbi.nlm.nih.gov/nuccore/NG_023319.2 (Year: 2018).*
GenBank accession No. NG_023302.1 [online]. GenBank, [2017] [retrieved on May 1, 2025]. Retrieved from: https://www.ncbi.nlm.nih.gov/nuccore/NG_023302.1 (Year: 2017).*
Houillier, IDH1 or IDH2 mutations predict longer survival and response to temozolomide in low-grade gliomas, Neurology, Oct. 2010, 75, 1560-1566 (Year: 2010).*
Juppner, Functional properties of the PTH/PTHrP receptor, Bone, Aug. 1995, S39-S42 (Year: 1995).*
Shaw, MGMT in TMZ-based glioma therapy: Multifaceted insights and clinical trial perspectives, Biochimica et Biophysica Acta ( BBA)—Molecular Cell Research, Mar. 2024, 1871, 1-19 (Year: 2024).*
Picca, The clinical use of IDH1 and IDH2 mutations in gliomas, HAL Open Science, Jan. 2019, 1-12 (Year: 2019).*
Extended European Search Report for EP application No. 20873930.0, mailed on Oct. 10, 2023, 21 pages.
Yan, et al., "IDH1 and IDH2 Mutations in Gliomas", the New England Journal of Medicine, Feb. 19, 2009, pp. 765-773.
Weller, et al., "European Association for Neuro-Oncology (EANO) guideline on the diagnosis and treatment of adult astrocytic and oligodendroglial gliomas," The Lancet Oncology, vol. 18, No. 6, May 5, 2017, 15 pages.
Malmstrom, et al., "Temozolomide versus standard 6-week radiotherapy versus hypofractionated radiotherapy in patients older than 60 years with glioblastoma: the Nordic randomised, phase 3 trial," The Lancet Oncology, Aug. 7, 2012, 11 pages.
Mansouri, et al., "MGMT promoter methylation status testing to guide therapy for glioblastoma: refining the approach based on emerging evidence and current challenges," Neuro-Oncology, vol. 21, No. 2, Sep. 5, 2018, 12 pages.

(Continued)

*Primary Examiner* — Anne M. Gussow
*Assistant Examiner* — Allison E Schloop
(74) *Attorney, Agent, or Firm* — Polsinelli PC

(57) ABSTRACT

The present disclosure relates to a method to detect simultaneously mutations and methylation levels in a biological sample of a subject. In particular the present disclosure is directed to a method for diagnosing a central nervous system tumor such as a diffuse glioma, in a subject and comprises the steps of—determining at the same time the presence or absence of a mutation and methylation levels in one or more regions of interest.

22 Claims, 14 Drawing Sheets
(14 of 14 Drawing Sheet(s) Filed in Color)

Specification includes a Sequence Listing.

(56) References Cited

OTHER PUBLICATIONS

Louis, et al., "The 2016 World Health Organization Classification of Tumors of the Central Nervous System: a summar," ACTA Neuropathologica, vol. 131, No. 6, May 9, 2016, 18 pages.
Watson, et al., "Cas9-based enrichment and single-molecule sequencing for precise characterization of genomic duplications," Laboratory Investigation, vol. 100, No. 1, Jul. 4, 2019, 12 pages.
Gilpatrick, et al., "Targeted Nanopore Sequencing with Cas9 for studies of methylation, structural variants and mutations," bioRxiv, Jun. 4, 2019, 14 pages.
Tsai, et al., "Amplification-free, CRISPR-Cas9 Targeted Enrichment and SMRT Sequencing of Repeat-Expansion Disease Causative Genomic Regions," Oct. 16, 2017, bioRxiv, 26 pages.
Stevens, et al., "A novel CRISPR/Cas9 associated technology for sequence-specific nucleic acid enrichment," PLOS ONE, vol. 14, No. 4, Apr. 18, 2019, 12 pages.
Gupta, et al., "Molecular markers of glioma: an update on recent progress and perspectives," Journal of Cancer Research and Clinical Oncology, vol. 138. No. 12, Oct. 6, 2012, 11 pages.
Scheie, et al., "Biomarkers in tumors of the central nervous system—a review," APMIS, vol. 127, No. 5, Feb. 10, 2019, 23 pages.
Bhavya, et al., "To be Wild or Mutant: Role of Isocitrate Dehydrogenase 1 (IDH1) and 2-Hydroxy Glutarate (2-HG) in Gliomagenesis and Treatment Outcome in Glioma," Cellular and Molecular Neurobiology, vol. 40, No. 1, Sep. 4, 2019, 11 pages.
Office Action issued Sep. 19, 2023 in related Canadian Application No. 3151627, 5 pages.
Strobel, Temozolomide and Other Alkylating Agents in Glioblastoma Therapy, Biomedicines, Sep. 9, 2019, 10.3390/biomedicines7030069, 17 pages.
International Search Report and Written Opinion issued Jan. 27, 2021 in related International Application No. PCT/US20/55256, 11 pages.
David Scheie et al., APMIS, Feb. 10, 2019, vol. 127, pp. 265-287.
Pierre Bady et al., Acta Neuropathologica, 2018, vol. 135, pp. 601-615.
Bharathan Bhavya et al., Cellular and Molecular Neurobiology, Sep. 4, 2019, vol. 40, pp. 53-63.

* cited by examiner

*Based on Sanger method, CLIA lab reports "mutation detected" or "no mutation".

SEQUENCE LISTING

<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: SYNTHESIZED

<400> SEQUENCE: 1
atgaggggcc cactaattga 20

<210> SEQ ID NO 2
<211> LENGTH: 20
<212> TYPE: DNA
<213> ORGANISM: Artificial Sequence
<220> FEATURE:
<223> OTHER INFORMATION: SYNTHESIZED

<400> SEQUENCE: 2
acctgagtat agctccgtac 20

<210> SEQ ID NO 3
<211> LENGTH: 20
<212> TYPE: DNA
<213> ORGANISM: Artificial Sequence
<220> FEATURE:
<223> OTHER INFORMATION: SYNTHESIZED

<400> SEQUENCE: 3
acagtccatg aatcaacctg 20

<210> SEQ ID NO 4
<211> LENGTH: 20
<212> TYPE: DNA
<213> ORGANISM: Artificial Sequence
<220> FEATURE:
<223> OTHER INFORMATION: SYNTHESIZED

<400> SEQUENCE: 4
ggcaccatac gaaatattct 20

<210> SEQ ID NO 5
<211> LENGTH: 20
<212> TYPE: DNA
<213> ORGANISM: Artificial Sequence
<220> FEATURE:
<223> OTHER INFORMATION: SYNTHESIZED

<400> SEQUENCE: 5
gctaggcgag gagctccagt 20

<210> SEQ ID NO 6
<211> LENGTH: 20
<212> TYPE: DNA
<213> ORGANISM: Artificial Sequence
<220> FEATURE:
<223> OTHER INFORMATION: SYNTHESIZED

<400> SEQUENCE: 6
gctgttgggg ccgctctcga 20

USE OF SIMULTANEOUS MARKER DETECTION FOR ASSESSING DIFFUSE GLIOMA AND RESPONSIVENESS TO TREATMENT

CROSS REFERENCE TO RELATED APPLICATIONS

This application claims benefit of International Application No. PCT/US2020/055256, filed Oct. 12, 2020, which claims priority from U.S. Provisional Application Ser. No. 62/914,141 filed on Oct. 11, 2019, the disclosures of which are incorporated herein by reference in their entirety.

FIELD OF THE TECHNOLOGY

This present disclosure generally relates to methods for detection of diffuse gliomas and assessing responsiveness to treatment in a biological sample of a subject.

REFERENCE TO SEQUENCE LISTING

This application contains a Sequence Listing that has been submitted in ASCII format via EFS-Web and is hereby incorporated by reference in its entirety. The ASCII copy, created on Oct. 12, 2020, is named 663400_Sequnce-Listing_ST25, and is 1,411 bytes in size.

BACKGROUND

Diffuse gliomas (DG) comprise 80% of primary malignant central nervous system tumors in adults and traditionally were diagnosed with pathological criteria to define histological type (e.g., astrocytoma, oligodendroglioma, or oligoastrocytoma) and malignancy grade (e.g., grades I-IV). In 2016, the World Health Organization (WHO) diagnostic guidelines incorporated molecular markers into the classification of DGs. Many of these diagnostic biomarkers also serve as prognostic indicators, and the neuro-oncology community has supported this integration of molecular markers into clinical practice. However, to date, there is wide variability in biomarker assessment because molecular techniques and test validity are inconsistent throughout the world and even within geographic regions. Therefore, the use of novel sequencing techniques that can assess multiple biomarkers simultaneously is an attractive option to overcome current clinical practice limitations.

Therefore, a need in the art exists for sequencing techniques that can assess multiple biomarkers simultaneously to guide physicians and patients in the decision-making process during treatment and care of central nervous system tumors.

SUMMARY

Among the various aspects of the present disclosure is the provision of methods for detecting a diffuse glioma in a subject by obtaining a biological sample for the subject; isolating genomic DNA from the sample; detecting simultaneously the presence or absence of a mutation and methylation levels in one or more regions of interest of the genomic DNA; comparing the presence or absence of the mutation and the methylation levels of the one or more regions of interest with a reference value; classifying the subject as having a diffuse glioma when the measured presence or absence of a mutation and the methylation levels deviate from the reference value.

In some embodiments, the methods include treating the genomic DNA after isolation to dephosphorylate the free DNA ends. In some embodiments, the DNA is treated with a phosphatase.

In another aspect, the methods comprise contacting the DNA is with a nuclease to generate targeted double strand breaks, thereby generating one or more regions of interest. In exemplary embodiments, one or more regions of interest include IDH1, IDH2, and MGMT genes, including 5' and 3' flanking regions of said genes. In some embodiments, the targeted double strand breaks are generated with CRISPR. In exemplary embodiments, the CRISPR crRNAs for MGMT comprise SEQ ID NOs:1-2, the CRISPR crRNAs for IDH1 comprise SEQ ID NOs: 3-4, and the CRISPR crRNAs for IDH2 comprise SEQ ID NOs: 5-6.

In some embodiments, the methods include modifying the free ends of the regions of interest after cutting with the nuclease to aide in the ligation of sequencing adaptors. Thus, in some embodiments, the methods include ligating one or more sequencing adaptor molecules to the one or more regions of interest and sequencing the regions of interest. In a particular aspect, nanopore sequencing is used.

The present disclosure also provides the provision of methods for assessing responsiveness to a therapeutic agent in a subject having or suspected of having a diffuse glioma by obtaining a biological sample for the subject; isolating genomic DNA from the sample; detecting simultaneously the presence or absence of a mutation and methylation levels in one or more regions of interest of the genomic DNA; comparing the presence or absence of the mutation and the methylation levels of the one or more regions of interest with a reference value; assessing therapy responsiveness based one the presence or absence of a mutation and the level of methylation.

In some embodiments, the methods include treating the genomic DNA after isolation to dephosphorylate the free DNA ends. In some embodiments, the DNA is treated with a phosphatase.

In another aspect, the methods comprise contacting the DNA is with a nuclease to generate targeted double strand breaks, thereby generating one or more regions of interest. In exemplary embodiments, one or more regions of interest include IDH1, IDH2, and MGMT genes, including 5' and 3' flanking regions of said genes. In some embodiments, the targeted double strand breaks are generated with CRISPR. In exemplary embodiments, the CRISPR crRNAs for MGMT comprise SEQ ID NOs:1-2, the CRISPR crRNAs for IDH1 comprise SEQ ID NOs: 3-4, and the CRISPR crRNAs for IDH2 comprise SEQ ID NOs: 5-6.

In some embodiments, the methods include modifying the free ends of the regions of interest after cutting with the nuclease to aide in the ligation of sequencing adaptors. Thus, in some embodiments, the methods include ligating one or more sequencing adaptor molecules to the one or more regions of interest and sequencing the regions of interest. In a particular aspect, nanopore sequencing is used.

In some embodiments, the methods include assessing the responsiveness to TMZ.

Other objects and features will be in part apparent and in part pointed out hereinafter.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 1A shows genotyping of IDH1 wild type, IDH2 wild type, IDH2 R172K mutation, and IDH1 R132G mutation. Exon 4 of IDH1 and IDH2 were PCR amplified and sequenced with nanopore technology. Nanopolish correctly genotyped all samples. FIG. 1B shows observed and expected CpG methylation percentage detected on methylated and unmethylated DNA standards. Standards that were 100% methylated or 0% methylated on CpGs were sequenced, and methylation calling was performed with Nanopolish. Data were generated for 10, 25, 50%, or 75% methylated CpGs by randomly sampling reads from each standard; at 20 depth coverage (20×), methylation levels of 0, 25, 50, 75, and 100% could be distinguished. Data represent the median, with 25th and 75th percentiles. Pairwise t-test with Bonferroni correction **** P<0.0001. Thus, 20× was used as the theoretical limit of detection in this study. FIG. 1C shows guide RNA (crRNA) for 3 target loci (MGMT (SEQ ID NOs:1-2), IDH1 (SEQ ID NOs:3-4), and IDH2 (SEQ ID NOs:5-6)) were designed and used for nanopore Cas9-targeted sequencing (nCATS) with the MinION device. Various types of sample were used for testing the feasibility of nCATS to assay methylation and mutations. GBM, glioblastoma; TMZ, temozolomide. FIG. 1D shows the median coverage of each loci for 10 samples.

FIG. 2A shows methylation was assayed by pyrosequencing and nCATS in 2 DNA standards: CpG methylated (MetCtrl) and unmethylated (UnMetCtrl). FIG. 2B shows methylation was assayed in DNA extracted from 4 glioblastoma cell lines: U87, U251, T98G, and LN18. Correlation (r) of methylation level between nCATS and pyrosequencing was calculated with P-value. Each yellow point is an individual CpG. FIG. 2C shows methylation pattern was assayed by pyrosequencing, MassARRAY, and nCATS in 4 IDH-mutant clinical samples. Correlation (r) of methylation level between nCATS and pyrosequencing was calculated with P-value. Each yellow point is an individual CpG. FIG. 2D shows IDH mutations were detected with the nCATS, Illumina, and Sanger sequencing platforms. IDH1 mutations were accurately detected in 3 patients (blue rows), and IDH2 mutation was detected in 1 patient (orange row). The pie charts and percentages indicate allele frequency detected by each method.

FIG. 3A shows MGMT gene expression was measured with qRT-PCR in 4 cell lines and 4 IDH-mutant tumor samples. Data are the mean±SD (3 technical replicates). FIG. 3B shows percent methylation of 12 clinically relevant CpG sites within MGMT exon 1. FIG. 3C shows correlation between MGMT expression and methylation detected by pyrosequencing vs. nCATS. Each yellow point is an individual sample. FIG. 3D shows a heat map and hierarchical clustering of percent methylation of the exon 1 CpGs and a portion of the intron 1 CpGs. Selected CpGs (r>0.7 or r<–0.7) were used for clustering. FIG. 3E shows the correlation between MGMT expression and exon 1 methylation and between MGMT expression and intron 1 methylation FIG. 4A shows MGMT gene expression in 4 IDH wild type samples by qRT-PCR. Data are the mean±SD (3 technical replicates). FIG. 4B shows the methylation pattern by nCATS and MassARRAY. FIG. 4C shows the correlation between MGMT expression and exon 1 methylation and between MGMT expression and intron 1 methylation. FIG. 4D shows SNVs in MGMT and IDH1/2 were assayed with nCATS and Illumina sequencing in tumor and saliva samples from 6 patients. Data were plotted with trackViewer. No data were available for P785 and P816.

DETAILED DESCRIPTION

Figure 1A:
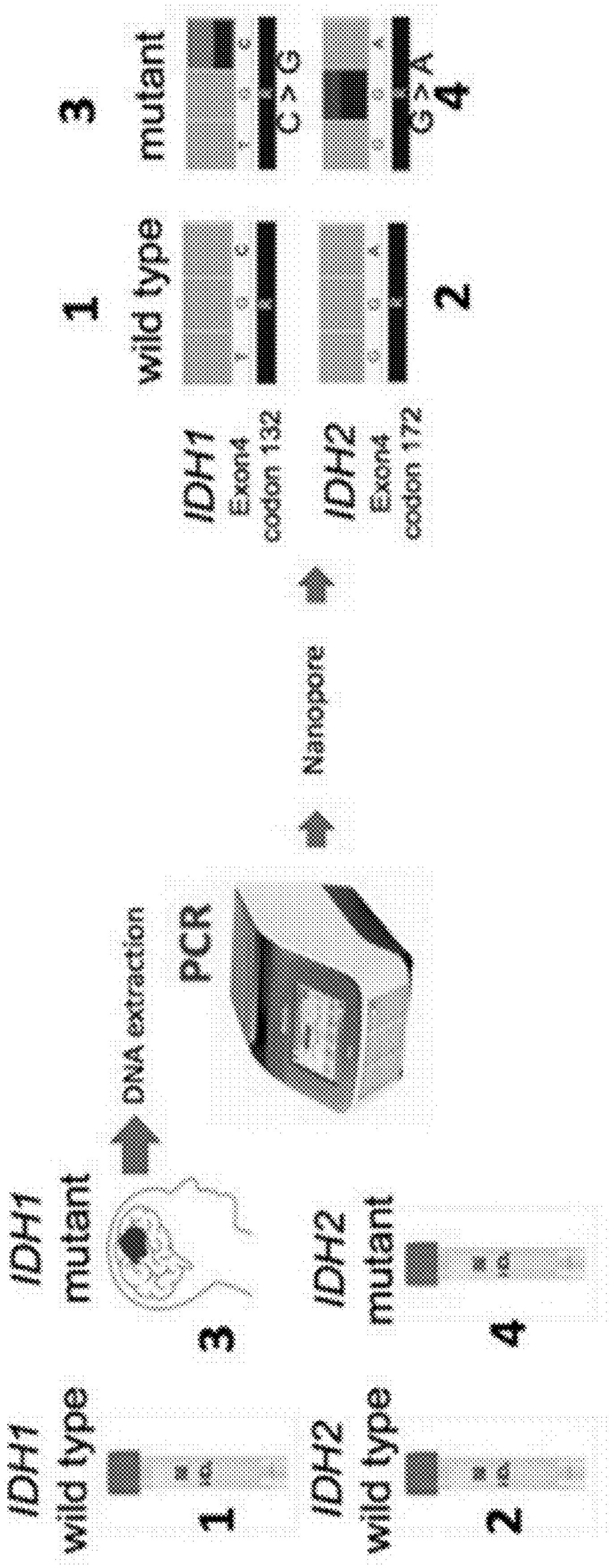
FIG. 1A-1D show mutation and methylation assessments with well-characterized samples was used to develop the nCATS workflow.

The present disclosure is based, at least in part, on the discovery that long-read nanopore-based sequencing technique is capable of simultaneously detecting IDH mutation status and MGMT methylation levels in a biological sample obtained from a subject. Currently, these biomarkers are assayed separately, and results can take days to weeks. As shown herein, the use of nanopore Cas9-targeted sequencing (nCATS) to identify IDH1 and IDH2 mutations within 36 h, thus the presently disclosed approach represents an improvement over currently used clinical methods. nCATS was also shown to be useful to simultaneously provide high-resolution evaluation of MGMT methylation levels not only at the promoter region, as with currently used methods, but also at CpGs across the proximal promoter region, the entirety of exon 1, and a portion of intron 1. Interestingly, when the methylation levels of all CpGs was compared to MGMT expression a positive correlation between intron 1 methylation and MGMT expression was observed. Finally, single nucleotide variants in 3 target loci were identified. This disclosure demonstrates the feasibility of using nCATS as a clinical tool for cancer precision medicine.

Altogether, the present disclosure provides multiple lines of evidence showing the presently disclosed method to be useful in the detection and prognosis of central nervous system tumors. Thus, the present disclosure encompasses use of the methods to simultaneously detect IDH mutation status and MGMT methylation levels in a biological sample to diagnose central nervous system tumors such as diffuse gilomas, guide treatment decisions, monitor disease progression, and evaluate the clinical efficacy of certain therapeutic interventions. Other aspects and iterations of the invention are described more thoroughly below.

I. Methods

One aspect of the present disclosure encompasses a method for diagnosing a tumors of the central nervous system in a subject, comprising the step of: determining simultaneously the mutation and methylation levels of one or more regions of interest in a biological sample (e.g. a biopsy) of said subject; wherein the presence of mutation and/or level of methylation of said one or more regions of interest is indicative for the disease. In some embodiments, the central nervous system tumor is a diffuse glioma. A Diffuse glioma according to the disclosure is a term used to encompass a variety of tumors of the central nervous system, which histologically appear similar to glial cells, such as astrocytomas, oligodendrogliomas and oligoastrocytomas, ranging from WHO grade II to grade IV tumors.

Certain mutations and/or methylation levels may be present in samples of a diseased subject compared to samples from healthy subjects or relative to a reference values. Therefore, the present disclosure encompasses determining the "presence" or "absence" of a one or more genomic mutations of a region of interest and/or the determining genomic methylation levels of a region of interest; and comparing the determined level to a reference level. Thus, the present disclosure provides the steps of determining presence or absence of a genomic mutations of one or more regions of interest and determining genomic methylation levels of one or more regions of interest; wherein the presence of one or more mutations and/or differing levels between the determined and the reference methylation levels are indicative for the disease. Hence, the invention also relates to a method for diagnosing a tumors of the central nervous system, determining responsiveness to a therapeutic agent, and monitoring the progression of tumors of the central nervous system, comprising the steps of: determining presence or absence of a of one or more genomic mutations in one or more regions of interest and determining genomic methylation levels in one or more regions of interest; wherein the presence of one or more mutations and/or differing levels between the determined and the reference methylation levels are indicative for the disease, responsiveness to a therapeutic agent or disease progression.

The methods as disclosed herein generally comprise providing or having been provided a biological sample. As used herein, the term "biological sample" means a biological material isolated from a subject. Any biological sample containing any genetic material suitable for detecting one or more genomic mutations and/or methylation levels in one or more regions of interest and may comprise cellular and/or non-cellular material obtained from the subject is suitable. Non-limiting examples include blood, plasma, serum, urine, and tissue. Frequently the sample will be a "clinical sample" which is a sample derived from a patient. Typical clinical samples include, but are not limited to, bodily fluid samples such as synovial fluid, sputum, blood, urine, blood plasma, blood serum, sweat, mucous, saliva, lymph, bronchial aspirates, peritoneal fluid, cerebrospinal fluid, and pleural fluid, and tissues samples, tissue or fine needle biopsy samples and abscesses or cells therefrom. Biological samples may also include sections of tissues, such as frozen sections or formalin fixed sections taken for histological purposes. In some embodiments, the biological sample is selected from saliva or brain tissues.

A "sample" may also be a sample originating from a biochemical or chemical reaction such as the product of an amplification reaction. Liquid samples may be subjected to one or more pre-treatments prior to use in the present disclosure. Such pre-treatments include, but are not limited to dilution, filtration, centrifugation, concentration, sedimentation, precipitation or dialysis. Pre-treatments may also include the addition of chemical or biochemical substances to the solution, e.g. in order to stabilize the sample and the contained nucleic acids, in particular the genomic DNA. Such addition of chemical or biochemical substances include acids, bases, buffers, salts, solvents, reactive dyes, detergents, emulsifiers, or chelators, like EDTA. The sample may for instance be taken and directly mixed with such substances. In one embodiment, substances are added to the sample in order to stabilize the sample until onset of analysis. "Stabilizing" in this context means prevention of degradation of the genomic regions of interest to be determined. Preferred stabilizers in this context are EDTA, e.g. K2EDTA, DNase inhibitors, alcohols e.g. ethanol and isopropanol, agents used to salt out proteins (such as RNAlater). In some embodiments, the methods do not include bisulfate modification. In preferred embodiments, genomic DNA is extracted from the biological sample and the sample comprising the extracted genomic DNA treated to dephosphorylate all of the free DNA ends. For example, the gDNA is treated with a phosphatase, such as calf intestinal phosphatase (NEB) to reduce dephosphorylate all of the free DNA ends.

As will be appreciated by a skilled artisan, the method of collecting a biological sample can and will vary depending upon the nature of the biological sample and the type of analysis to be performed. Any of a variety of methods generally known in the art may be utilized to collect a biological sample. Generally speaking, the method preferably maintains the integrity of the sample such that the genomic regions of interest can be accurately detected according to the disclosure.

In some embodiments, a single sample is obtained from a subject to detect one or more genomic regions of interest in the sample. Alternatively, one or more genomic regions of interest may be detected in samples obtained over time from a subject. As such, more than one sample may be collected from a subject over time. For instance, 2, 3, 4, 5, 6, 7, 8, 9, 10, 11, 12, 13, 14, 15, 16 or more samples may be collected from a subject over time. In some embodiments, 2, 3, 4, 5, or 6 samples are collected from a subject over time. In other embodiments, 6, 7, 8, 9, or 10 samples are collected from a subject over time. In yet other embodiments, 10, 11, 12, 13, or 14 samples are collected from a subject over time. In other embodiments, 14, 15, 16 or more samples are collected from a subject over time.

When more than one sample is collected from a subject over time, samples may be collected every 0.5, 1, 2, 3, 4, 5, 6, 7, 8, 9, 10, 11, 12 or more hours. In some embodiments, samples are collected every 0.5, 1, 2, 3, or 4 hours. In other embodiments, samples are collected every 4, 5, 6, or 7 hours. In yet other embodiments, samples are collected every 7, 8, 9, or 10 hours. In other embodiments, samples are collected every 10, 11, 12 or more hours. Additionally, samples may be collected every 1, 2, 3, 4, 5, 6, 7, 8, 9, 10, 11, 12 or more days. In some embodiments, a sample is collected about every 6 days. In some embodiments, samples are collected every 1, 2, 3, 4, or 5 days. In other embodiments, samples are collected every 5, 6, 7, 8, or 9 days. In yet other embodiments, samples are collected every 9, 10, 11, 12 or more days.

In some embodiments the sample comprises a nucleic acid or nucleic acids. The term "nucleic acid" is here used in its broadest sense and comprises ribonucleic acids (RNA) and deoxyribonucleic acids (DNA) from all possible sources, in all lengths and configurations, such as double stranded, single stranded, circular, linear or branched. All sub-units and subtypes are also comprised, such as monomeric nucleotides, oligomers, plasmids, viral and bacterial nucleic acids, as well as genomic and non-genomic DNA and RNA from the subject, circular RNA (circRNA), messenger RNA (mRNA) in processed and unprocessed form, transfer RNA (tRNA), heterogeneous nuclear RNA (hnRNA), ribosomal RNA (rRNA), complementary DNA (cDNA) as well as all other conceivable nucleic acids. However, in the most preferred embodiment the sample comprises genomic DNA.

Generally speaking, the methods as disclosed herein include within the detection step, generating targeted double strand breaks in the genomic DNA so as to isolate a genomic region of interest from the remaining genomic DNA. The targeted double strand breaks are upstream and downstream of a genomic region of interest. Thus, the methods provided herein are useful for interrogating a continuous genomic region, i.e. a continuous length of DNA between the 5' and 3' targeted double strand breaks. Such a continuous genomic region may comprise small portions, i.e., genomic sequences of about 50 kb, up to the entire chromosome or the entire genome. In one embodiment, the compositions and methods are useful in interrogating a functional element of the genome. A functional element typically encompasses a limited region of the genome, such as a region of 50, 60, 70, 80, 90 to 100 kb of genomic DNA. In one embodiment, the methods described herein comprise the interrogation of non-coding genomic regions, such as regions 5' and 3' of the coding region of a gene of interest, in addition to the coding regions of a gene of interest. The methods allow the identification of targets in the 5' and 3' region and coding region of a gene which may affect a phenotypic change only under particular circumstances or only for particular cells or tissues in an organism.

In certain embodiments, the genomic region of interest comprises a transcription factor binding site, a region of DNase I hypersensitivity, a transcription enhancer or repressor element, a chromosome, or other intergenic region containing sequence with biochemical activity. In other embodiments, the genomic region of interest comprises an epigenetic signature for a particular disease or disorder. Additionally, or alternatively, the genomic region of interest may comprise an epigenetic insulator. In other embodiments, a genomic region of interest comprises two or more continuous genomic regions that physically interact. In still other embodiments, the genomic region of interest comprises one or more sites susceptible to one or more of histone acetylation, histone methylation, histone ubiquitination, histone phosphorylation, DNA methylation, or a lack thereof.

Examples of genomic regions of interest for interrogation using the methods described herein include regions comprising, or located 5' or 3' of, a gene associated with a signaling biochemical pathway, e.g., a signaling biochemical pathway associated gene or polynucleotide. Examples of genomic regions include regions comprising, or located within the gene coding region and/or 5' and/or 3' of, a disease associated gene or polynucleotide. In one embodiment, the region located 5' and/or 3' of a gene refers to a genomic region of a genome or a chromosome from a first nucleotide of the genome or chromosome to a second nucleotide of the genome or chromosome. The second nucleotide is located between the first nucleotide and the gene in the genome or chromosome. The first nucleotide is about 100 bp, about 200 bp, about 300 bp, about 400 bp, about bp, about 600 bp, about 700 bp, about 800 bp, about 900 bp, about 1 kb, about 2 kb, about 3 kb, about 4 kb, about 5 kb, about 6 kb, about 7 kb, about 8 kb, about 9 kb, about 10 kb, about 15 kb, about 20 kb, about 30 kb, about 40 kb, about 50 kb, about 60 kb, about 70 kb, about 80 kb, about 90 kb, about 100 kb, about 150 kb, about 200 kb, about 250 kb, about 300 kb, about 350 kb, about 400 kb, about 450 kb, about 500 kb, about 550 kb, about 600 kb, about 650 kb, about 700 kb, about 750 kb, about 800 kb, about 850 kb, about 900 kb, about 950 kb, or about 1 mb, 5' or 3' to the gene. A "disease-associated" gene or polynucleotide refers to any gene or polynucleotide which yields transcription or translation products at an abnormal level or in an abnormal form in cells derived from a disease-affected tissue compared with tissues or cells of a non-disease control. Another embodiment of a disease-associated gene is a gene that becomes expressed at an abnormally high level; it may be a gene that becomes expressed at an abnormally low level. The altered expression correlates with the occurrence and/or progression of the disease. The transcribed or translated products may be known or unknown, and may be expressed at a normal or abnormal level. Sites of DNA hypersensitivity, transcription factor binding sites, and epigenetic markers of a gene of interest can be determined by accessing publicly available data bases. In a preferred embodiment, the genomic region of interest comprises the IDH1 gene, including bases which are 5' or 3' to the gene. In a preferred embodiment, the genomic region of interest comprises the IDH2 gene, including bases which are 5' or 3' to the gene. In a preferred embodiment, the genomic region of interest comprises the MGMT gene, including bases which are 5' or 3' to the gene.

Techniques such as CRISPR (particularly using Cas9 and guide RNA), editing with zinc finger nucleases (ZFNs) and transcription activator-like effector nucleases (TALENs) may be used to generate the double strand breaks according to the disclosure. Targeted genome modification (interchangeable with "targeted genomic editing" or "targeted genetic editing") enables insertion, deletion, and/or substitution at pre-selected sites in the genome. According to the present disclosure, genomic DNA undergoes targeted modification by removing one or more regions of interest from the genomic DNA. Targeted modification can be achieved either through a nuclease-dependent approach. Thus, targeted modification could be achieved with higher frequency through specific introduction of double strand breaks (DSBs) by specific rare-cutting endonucleases. In some embodiments, non-limiting examples of targeted nucleases include naturally occurring and recombinant nucleases; CRISPR related nucleases from families including cas, cpf, cse, csy, csn, csd, cst, csh, csa, csm, and cmr; restriction endonucleases; meganucleases; homing endonucleases, and the like. In an exemplary embodiment, CRISPR/Cas9 requires two major components: (1) a Cas9 endonuclease and (2) the crRNA-tracrRNA complex. When co-expressed, the two components form a complex that is recruited to a target DNA sequence comprising PAM and a seeding region near PAM. The crRNA and tracrRNA can be combined to form a chimeric guide RNA (gRNA) to guide Cas9 to target selected sequences.

Besides the CRISPR method disclosed herein, additional genomic modification methods as known in the art can also be used for introducing double strand breaks in isolated genomic DNA. Some examples include zinc finger nuclease (ZFN), transcription activator-like effector nucleases (TALEN), restriction endonucleases, meganucleases homing endonucleases, and the like.

ZFNs are targeted nucleases comprising a nuclease fused to a zinc finger DNA binding domain (ZFBD), which is a polypeptide domain that binds DNA in a sequence-specific manner through one or more zinc fingers. A zinc finger is a domain of about 30 amino acids within the zinc finger binding domain whose structure is stabilized through coordination of a zinc ion. Examples of zinc fingers include, but not limited to, C2H2 zinc fingers, C3H zinc fingers, and C4 zinc fingers. A designed zinc finger domain is a domain not occurring in nature whose design/composition results principally from rational criteria, e.g., application of substitution rules and computerized algorithms for processing information in a database storing information of existing ZFP designs and binding data. See, for example, U.S. Pat. Nos. 6,140,081; 6,453,242; and 6,534,261; see also WO 98/53058; WO 98/53059; WO 98/53060; WO 02/016536 and WO 03/016496. A selected zinc finger domain is a domain not found in nature whose production results primarily from an empirical process such as phage display, interaction trap or hybrid selection. ZFNs are described in greater detail in U.S. Pat. Nos. 7,888,121 and 7,972,854. The most recognized example of a ZFN is a fusion of the FokI nuclease with a zinc finger DNA binding domain.

A TALEN is a targeted nuclease comprising a nuclease fused to a TAL effector DNA binding domain. A "transcription activator-like effector DNA binding domain", "TAL effector DNA binding domain", or "TALE DNA binding domain" is a polypeptide domain of TAL effector proteins that is responsible for binding of the TAL effector protein to DNA. TAL effector proteins are secreted by plant pathogens of the genus *Xanthomonas* during infection. These proteins enter the nucleus of the plant cell, bind effector-specific DNA sequences via their DNA binding domain, and activate gene transcription at these sequences via their transactivation domains. TAL effector DNA binding domain specificity depends on an effector-variable number of imperfect 34 amino acid repeats, which comprise polymorphisms at select repeat positions called repeat variable-diresidues (RVD). TALENs are described in greater detail in US Patent Application No. 2011/0145940. The most recognized example of a TALEN in the art is a fusion polypeptide of the FokI nuclease to a TAL effector DNA binding domain.

After the targeted double strand breaks occur, isolating the one or more regions of interest from the remaining genomic DNA, an enrichment of free 5' phosphate sites occur at the cleavage site. Thus, the unique 5' phosphate sites surrounding the region of interest can be modified to allow ligation to a sequencing adapter molecule. In a non-limiting example, an adenine (A)-tail can be added to the 3' ends of cut DNA fragments using a DNA polymerase, such as Taq polymerase and dATP. The A overhang can pair with a T overhang of the sequencing adapters. Both adapter-ligated DNA and blocked DNA can be added to a flow cell for sequencing. The excess unligated adapters are optionally removed prior to sequencing. In preferred embodiments, a nanopore flow cell, such as minion or Fongle is used. Nanopore sequencing is a unique, scalable technology that enables direct, real-time analysis of long DNA or RNA fragments. It works by monitoring changes to an electrical current as nucleic acids are passed through a protein nanopore. The resulting signal is decoded to provide the specific DNA or RNA sequence information.

"Presence" or "absence" of one or more mutations or methylation levels in connection with the present disclosure means that the mutation, such as a single nucleotide mutation, or methylation levels is present at levels above a certain threshold or below a certain threshold, respectively. In case the threshold is "0" this would mean that "presence" is the actual presence of a mutation in the sample and "absence" is the actual absence. However, "presence" in context with the present disclosure may also mean that the respective methylation level is present at a level above a threshold, e.g. the levels determined in a control, "absence" in this context then means that the level of the methylation is at or below the certain threshold.

The term "reference level" relates to a level to which the determined level is compared in order to allow the distinction between "presence" or "absence" of a mutation or level of methylation. The reference level includes the level which is determinant for the deductive step of making the actual diagnose or determining efficacy of a therapeutic agent. The reference level in a preferred embodiment relates to the level of methylation of the region of interest or mutational status in a healthy subject or a population of healthy subjects, i.e. a subject not having the disease to be diagnosed, e.g. not having a central nervous system tumor, such as diffuse glioma. The skilled person with the disclosure of the present application is in the position to determine suited control levels using common statistical methods.

A "reference level" to a control region of interest may also mean a level of the methylation or mutational status that is indicative of the absence of a disease state or responsiveness to a therapeutic agent. In some embodiments, when the level of the methylation or mutational status in a subject is above the reference level it is indicative of the presence of a disease state or responsiveness to a therapeutic agent. In some embodiments, when the level of the methylation or mutational status in a subject is above the reference level it is indicative of the absence of a disease state or non-responsiveness to a therapeutic agent. In some embodiments, when the level of the methylation or mutational status in a subject is below the reference level indicative of the presence of a disease state or responsiveness to a therapeutic agent. In some embodiments, when the level of the methylation or mutational status in a subject is below the reference level it is indicative of the lack of a disease state or non-responsiveness to a therapeutic agent. In some embodiments, when the level of a methylation in a subject is within the reference level it indicatives either responsiveness or non-responsiveness to a therapeutic agent.

The mutational status and/or methylation levels of the one or more regions of interest may be analyzed in a number of fashions well known to a person skilled in the art. For example, each assay result obtained may be compared to a "normal" or "control" value, or a value indicating a particular disease or therapeutic outcome. A particular diagnosis/prognosis may depend upon the comparison of each assay result to such a value, which may be referred to as a diagnostic or prognostic "threshold". In certain embodiments, assays for one or more diagnostic or prognostic indicators are correlated to a condition or disease by merely the presence or absence of the mutation in the assay. For example, an assay can be designed so that a positive signal only occurs above a particular threshold level of interest, and below which level the assay provides no signal above background.

The skilled artisan will understand that associating a diagnostic or prognostic indicator, with a diagnosis or with a prognostic risk of a future clinical outcome is a statistical analysis. For example, a marker level of lower than X may signal that a patient is more likely to suffer from an adverse outcome than patients with a level more than or equal to X, as determined by a level of statistical significance. For another marker, a marker level of higher than X may signal that a patient is more likely to suffer from an adverse outcome than patients with a level less than or equal to X, as determined by a level of statistical significance. Additionally, a change in marker concentration from baseline levels may be reflective of patient prognosis, and the degree of change in marker level may be related to the severity of adverse events. Statistical significance is often determined by comparing two or more populations, and determining a confidence interval and/or a p value. See, e.g., Dowdy and Wearden, Statistics for Research, John Wiley & Sons, New York, 1983. Preferred confidence intervals of the invention are 90%, 95%, 97.5%, 98%, 99%, 99.5%, 99.9% and 99.99%, while preferred p values are 0.1, 0.05, 0.025, 0.02, 0.01, 0.005, 0.001, and 0.0001. Suitable threshold levels for the diagnosis of the disease can be determined for certain combinations. This can e.g. be done by grouping a reference population of patients according to their mutational status and/or levels of mehtyaltion into certain quantiles, e.g. quartiles, quintiles or even according to suitable percentiles. For each of the quantiles or groups above and below certain percentiles, hazard ratios can be calculated comparing the risk for an adverse outcome, i.e. a "disease" or "therapeutic outcomes", between those patients who have a certain disease and those who have not. In such a scenario, a hazard ratio (HR) above 1 indicates a higher risk for an adverse outcome for the patients. A HR below 1 indicates beneficial effects of a certain treatment in the group of patients. A HR around 1 (e.g. +/−0.1) indicates no elevated risk for the particular group of patients. By comparison of the HR between certain quantiles of patients with each other and with the HR of the overall population of patients, it is possible to identify those quantiles of patients who have an elevated risk and those who benefit from medication and thereby stratify subjects according to the present invention.

The skilled person is able to use sequencing techniques in connection with the present invention. Sequencing techniques include but are not limited to Maxam-Gilbert Sequencing, Sanger sequencing (chain-termination method using ddNTPs), and next generation sequencing methods, like massively parallel signature sequencing (MPSS), polony sequencing, 454 pyrosequencing, Illumina (Solexa) sequencing, SOLiD sequencing, or ion torrent semiconductor sequencing or single molecule, real-time technology sequencing (SMRT).

MGMT is a gene encoding O-6-methylguanine-DNA methyltransferase protein. MGMT is located on chromosome 10 (129467184-129768007 Chromosome location (bp)). Nucleic acid and peptide information with regards to MGMT can be found in publically available databases such as Ensembl (ENSG00000170430), Entrez gene (4255), and UniProt (P16455). As described herein, expression MGMT correlates with a subjects responsiveness to chemotherapeutic agents such as Temozolomide (TMZ). As described herein, it was found that MGMT expression negatively correlates with exon 1 methylation levels and MGMT expression positively correlates with methylation levels.

IDH1 is a gene encoding the isocitrate dehydrogenase (NADP(+)) 1, cytosolic protein. IDH1 is located on chromosome 2 (208236227-208266074 Chromosome location (bp)). Nucleic acid and peptide information with regards to IDH1 can be found in publically available databases such as Ensembl (ENSG00000138413), Entrez gene (3417), and UniProt (075874). IDH2 is a gene encoding the Isocitrate dehydrogenase (NADP(+)) 2, mitochondrial protein. IDH2 is located on chromosome 15 (90083045-90102504 Chromosome location (bp)). Nucleic acid and peptide information with regards to IDH1 can be found in publically available databases such as Ensembl (ENSG00000182054), Entrez gene (3418), and UniProt (P48735). As described herein, the presence or absence of mutations in IDH1 and/or IDH2 provide diagnostic information for determining the presence or absence of a diffuse glioma.

The one or more regions of interest disclosed herein encompass characteristic profiles which are identified in a biological sample obtained from a subject relative to a reference value as useful for making diagnostic and treatment decisions. See, e.g., the Examples below. In various embodiments, determining the mutational status and/or methylation levels of one or more regions of interest can be supplemented with diagnostic assays such as assays to determine presence, absence, amyloid plaques, advanced radiographic assays, and diagnostic assays.

In some embodiments, the methods may comprise determining the mutational status and/or methylation levels of at least 1 region of interest, at least 2 region of interest, at least 3 region of interest, at least 4 region of interest, at least 5 region of interest, at least 6 region of interest, at least 6 region of interest, at least 7 region of interest, at least 8 region of interest, at least 9 region of interest, at least 10 or more regions of interest.

An aspect of the present disclosure encompasses methods to detect a diffuse glioma in subjects comprising providing or having been provided a biological sample from a subject; detecting simultaneously the presence or absence of mutation and methylation levels in one or more regions of interest; comparing the presence or absence or mutation and the methylation levels of the one or more regions of interest with a reference value; diagnosing the subject as having a diffuse glioma when the measured presence or absence or mutation and the methylation levels deviate from the reference value. In some aspects, the detecting step may include one or more of the following: isolating genomic DNA from the sample, treating the genomic DNA to dephosphorylate the free DNA ends, introducing targeted double strand breaks in the genomic DNA to generate one or more regions of interest, modifying the free ends of the regions of interest to aide in the ligation of sequencing adaptors, ligating one or more sequencing adaptor molecules to the one or more regions of interest and sequencing the regions of interest. In some embodiments, nanopore sequencing is used. In some embodiments, the one or more regions of interest include the IDH1, IDH2, and MGMT genes, including the 5' and 3' regions flanking said genes.

In aspect of the present disclosure encompasses methods to determine responsiveness to a therapeutic agent in subject having or suspected of having a diffuse glioma, the method comprising providing or having been provided a biological sample from the subject; detecting simultaneously the presence or absence of mutation and methylation levels in one or more regions of interest; comparing the presence or absence or mutation and the methylation levels of the one or more regions of interest with a reference value; assessing the subject's responsiveness to the therapeutic agent when the measured presence or absence or mutation and the methylation levels deviate from the reference value. In some aspects, the detecting step may include one or more of the following: isolating genomic DNA from the sample, treating the genomic DNA to dephosphorylate the free DNA ends, introducing targeted double strand breaks in the genomic DNA to generate one or more regions of interest, modifying the free ends of the regions of interest to aide in the ligation of sequencing adaptors, ligating one or more sequencing adaptor molecules to the one or more regions of interest and sequencing the regions of interest. In some embodiments, nanopore sequencing is used. In some embodiments, the one or more regions of interest include the IDH1, IDH2, and MGMT genes, including the 5' and 3' regions flanking said genes. In some embodiment, the therapeutic agent is TMZ.

II. Treatment

Another aspect of the present disclosure is a method for treating a subject in need thereof. The terms "treat," "treating," or "treatment" as used herein, refers to the provision of medical care by a trained and licensed professional to a subject in need thereof. The medical care may be a diagnostic test, a therapeutic treatment, and/or a prophylactic or preventative measure. The object of therapeutic and prophylactic treatments is to prevent or slow down (lessen) an undesired physiological change or disease/disorder. Beneficial or desired clinical results of therapeutic or prophylactic treatments include, but are not limited to, alleviation of symptoms, diminishment of extent of disease, stabilized (i.e., not worsening) state of disease, a delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the disease, condition, or disorder as well as those prone to have the disease, condition or disorder or those in which the disease, condition or disorder is to be prevented. In some embodiments, a subject receiving treatment is asymptomatic. An “asymptomatic subject,” as used herein, refers to a subject that does not show any signs or symptoms of a central nervous system tumor. In other embodiments, a subject may exhibit signs or symptoms of central nervous system tumor (e.g., memory loss, changes in mood or behavior, pain, etc,).

One aspect of the present disclosure relates to methods for assessing responsiveness or non-responsiveness of a subject having or suspected of having a central nervous system tumor to be responsive or non-responsive to a therapeutic agent (e.g., chemotherapy such as TMZ or radiation) based on the detection of mutation and methylation levels in one or more regions of interest as disclosed herein. As used herein, assessing “responsiveness” or “non-responsiveness” to a therapeutic agent refers to the determination of the likelihood of a subject for responding or not responding to the therapeutic agent.

When more than one region of interest is investigated, as in the present methods, the mutational status and methylation levels of the ROIs can be processed by, e.g., a computational program to generate a profile, which can be represented by a number or numbers that characterize the pattern of the ROIs.

When a subject is determined to be responsive or non-responsive by any of the methods described, this subject could be subjected to a treatment for a central nervous system tumor, including any of the central nervous system tumor treatments known in the art and disclosed herein. In one aspect, a subject determined to be likely responsive using the methods described herein, the subject may then be administered an effective amount of chemotherapy or radiation for treating a central nervous system tumor. Non-limiting examples include TMZ.

In certain aspects, a therapeutically effective amount of a pharmaceutical composition may be administered to a subject. Administration is performed using standard effective techniques, including peripherally (i.e. not by administration into the central nervous system) or locally to the central nervous system. Peripheral administration includes but is not limited to oral, inhalation, intravenous, intraperitoneal, intra-articular, subcutaneous, pulmonary, transdermal, intramuscular, intranasal, buccal, sublingual, or suppository administration. Local administration, includes but is not limited to via a lumbar, intraventricular or intraparenchymal catheter or using a surgically implanted controlled release formulation. The route of administration may be dictated by the disease or condition to be treated.

Pharmaceutical compositions for effective administration are deliberately designed to be appropriate for the selected mode of administration, and pharmaceutically acceptable excipients such as compatible dispersing agents, buffers, surfactants, preservatives, solubilizing agents, isotonicity agents, stabilizing agents, and the like are used as appropriate. Remington’s Pharmaceutical Sciences, Mack Publishing Co., Easton Pa., 16Ed ISBN: 0-912734-04-3, latest edition, incorporated herein by reference in its entirety, provides a compendium of formulation techniques as are generally known to practitioners.

In each of the above embodiments, a pharmaceutical composition may comprise an imaging agent. Non-limiting examples of imaging agents include functional imaging agents (e.g. fluorodeoxyglucose, etc.) and molecular imaging agents (e.g., Pittsburgh compound B, florbetaben, florbetapir, flutemetamol, radionuclide-labeled antibodies, etc.).

In some embodiments, a minimal dose is administered, and dose is escalated in the absence of dose-limiting toxicity. Determination and adjustment of a therapeutically effective dose, as well as evaluation of when and how to make such adjustments, are known to those of ordinary skill in the art of medicine.

The frequency of dosing may be daily or once, twice, three times or more per week or per month, as needed as to effectively treat the symptoms. The timing of administration of the treatment relative to the disease itself and duration of treatment will be determined by the circumstances surrounding the case. Treatment could begin immediately, such as at the site of the injury as administered by emergency medical personnel. Treatment could begin in a hospital or clinic itself, or at a later time after discharge from the hospital or after being seen in an outpatient clinic. Duration of treatment could range from a single dose administered on a one-time basis to a life-long course of therapeutic treatments.

Typical dosage levels can be determined and optimized using standard clinical techniques and will be dependent on the mode of administration.

A subject may be a rodent, a human, a livestock animal, a companion animal, or a zoological animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas, and alpacas. In still another embodiment, the subject may be a companion animal. Non-limiting examples of companion animals may include pets such as dogs, cats, rabbits, and birds. In yet another embodiment, the subject may be a zoological animal. As used herein, a “zoological animal” refers to an animal that may be found in a zoo. Such animals may include non-human primates, large cats, wolves, and bears. In a preferred embodiment, the subject is a human.

III. Kits

Also provided are kits. Such kits can include an agent or composition described herein and, in certain embodiments, instructions for administration. Such kits can facilitate performance of the methods described herein. When supplied as a kit, the different components of the composition can be packaged in separate containers and admixed immediately before use. Components include, but are not limited to systems, assays, primers, or software. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, sterile saline or sterile each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like.

Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate, and/or may be supplied as an electronic-readable medium or video. Detailed instructions may not be physically associated with the kit; instead, a user may be directed to an Internet web site specified by the manufacturer or distributor of the kit.

A control sample or a reference sample as described herein can be a sample from a healthy subject or from a randomized group of subjects. A reference value can be used in place of a control or reference sample, which was previously obtained from a healthy subject or a group of healthy subject. A control sample or a reference sample can also be a sample with a known amount of a detectable compound or a spiked sample.

The methods and algorithms of the invention may be enclosed in a controller or processor. Furthermore, methods and algorithms of the present invention, can be embodied as a computer implemented method or methods for performing such computer-implemented method or methods, and can also be embodied in the form of a tangible or non-transitory computer readable storage medium containing a computer program or other machine-readable instructions (herein "computer program"), wherein when the computer program is loaded into a computer or other processor (herein "computer") and/or is executed by the computer, the computer becomes an apparatus for practicing the method or methods. Storage media for containing such computer program include, for example, floppy disks and diskettes, compact disk (CD)-ROMs (whether or not writeable), DVD digital disks, RAM and ROM memories, computer hard drives and back-up drives, external hard drives, "thumb" drives, and any other storage medium readable by a computer. The method or methods can also be embodied in the form of a computer program, for example, whether stored in a storage medium or transmitted over a transmission medium such as electrical conductors, fiber optics or other light conductors, or by electromagnetic radiation, wherein when the computer program is loaded into a computer and/or is executed by the computer, the computer becomes an apparatus for practicing the method or methods. The method or methods may be implemented on a general purpose microprocessor or on a digital processor specifically configured to practice the process or processes. When a general-purpose microprocessor is employed, the computer program code configures the circuitry of the microprocessor to create specific logic circuit arrangements. Storage medium readable by a computer includes medium being readable by a computer per se or by another machine that reads the computer instructions for providing those instructions to a computer for controlling its operation. Such machines may include, for example, machines for reading the storage media mentioned above.

General Techniques

The practice of the present disclosure will employ, unless otherwise indicated, conventional techniques of molecular biology (including recombinant techniques), microbiology, cell biology, biochemistry, and immunology, which are within the skill of the art. Such techniques are explained fully in the literature, such as Molecular Cloning: A Laboratory Manual, second edition (Sambrook, et al., 1989) Cold Spring Harbor Press; Oligonucleotide Synthesis (M. J. Gait, ed. 1984); Methods in Molecular Biology, Humana Press; Cell Biology: A Laboratory Notebook (J. E. Cellis, ed., 1989) Academic Press; Animal Cell Culture (R. I. Freshney, ed. 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds. 1993-8) J. Wiley and Sons; Methods in Enzymology (Academic Press, Inc.); Handbook of Experimental Immunology (D. M. Weir and C. C. Blackwell, eds.): Gene Transfer Vectors for Mammalian Cells (J. M. Miller and M. P. Calos, eds., 1987); Current Protocols in Molecular Biology (F. M. Ausubel, et al. eds. 1987); PCR: The Polymerase Chain Reaction, (Mullis, et al., eds. 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practice approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds. Harwood Academic Publishers, 1995); DNA Cloning: A practical Approach, Volumes I and II (D. N. Glover ed. 1985); Nucleic Acid Hybridization (B. D. Hames & S. J. Higgins eds. (1985»; Transcription and Translation (B. D. Hames & S. J. Higgins, eds. (1984»; Animal Cell Culture (R. I. Freshney, ed. (1986»; Immobilized Cells and Enzymes (IRL Press, (1986»; and B. Perbal, A practical Guide To Molecular Cloning (1984); F. M. Ausubel et al. (eds.).

So that the present disclosure may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

As used herein the term, "simultaneous" as it refers to the detection of IDH mutation and MGMT means detecting the aforementioned markers at the same time in a single reaction mixture. Thus, as described herein, the present disclosure demonstrates nCATS enables enrichment of genomic regions without amplification and quantitative analysis of methylation on native DNA, and identification of single nucleotide variants can be detected at the same time.

The term "about," as used herein, refers to variation of in the numerical quantity that can occur, for example, through typical measuring techniques and equipment, with respect to any quantifiable variable, including, but not limited to, mass, volume, time, distance, and amount. Further, given solid and liquid handling procedures used in the real world, there is certain inadvertent error and variation that is likely through differences in the manufacture, source, or purity of the ingredients used to make the compositions or carry out the methods and the like. The term "about" also encompasses these variations, which can be up to ±5%, but can also be ±4%, 3%, 2%, 1%, etc. Whether or not modified by the term "about," the claims include equivalents to the quantities.

When introducing elements of the present disclosure or the preferred aspects(s) thereof, the articles "a," "an," "the," and "said" are intended to mean that there are one or more of the elements. The terms "comprising," "including," and "having" are intended to be inclusive and mean that there may be additional elements other than the listed elements.

"Measuring" or "measurement," or alternatively "detecting" or "detection," means determining the presence, absence, quantity or amount (which can be an effective amount) of either a given substance within a clinical or subject-derived sample, including the derivation of qualitative or quantitative concentration levels of such substances, or otherwise determining the values or categorization of a subject's clinical parameters.

The terms "patient," "subject," "individual," and the like are used interchangeably herein, and refer to any animal or cells thereof whether in vitro or in situ, amenable to the methods described herein. In certain non-limiting embodiments, the patient, subject or individual is a human.

"Platform" or "technology" as used herein refers to an apparatus (e.g., instrument and associated parts, computer, computer-readable media comprising one or more databases as taught herein, reagents, etc.) that may be used to measure a signature, e.g., gene expression levels, in accordance with the present disclosure. Examples of platforms include, but are not limited to, an array platform, a thermal cycler platform (e.g., multiplexed and/or real-time PCR platform), a nucleic acid sequencing platform, a hybridization and multi-signal coded (e.g., fluorescence) detector platform, etc., a nucleic acid mass spectrometry platform, a magnetic resonance platform, and combinations thereof.

In some embodiments, the platform is configured to measure gene expression levels semi-quantitatively, that is, rather than measuring in discrete or absolute expression, the expression levels are measured as an estimate and/or relative to each other or a specified marker or markers (e.g., expression of another, "standard" or "reference," gene).

In some embodiments, semi-quantitative measuring includes "real-time PCR" by performing PCR cycles until a signal indicating the specified mRNA is detected, and using the number of PCR cycles needed until detection to provide the estimated or relative expression levels of the genes within the signature.

A real-time PCR platform includes, for example, a TaqMan® Low Density Array (TLDA), in which samples undergo multiplexed reverse transcription, followed by real-time PCR on an array card with a collection of wells in which real-time PCR is performed. A real-time PCR platform also includes, for example, a Biocartis Idylla™ sample-to-result technology, in which cells are lysed, DNA/RNA extracted and real-time PCR is performed and results detected. A real-time PCR platform also includes, for example, CyTOF analysis: CyTOF (Fludigm) is a recently introduced mass-cytometer capable of detecting up to 40 markers conjugated to heavy metals simultaneously on single cells.

A magnetic resonance platform includes, for example, T2 Biosystems® T2 Magnetic Resonance (T2MR®) technology, in which molecular targets may be identified in biological samples without the need for purification.

The terms "array," "microarray" and "micro array" are interchangeable and refer to an arrangement of a collection of nucleotide sequences presented on a substrate. Any type of array can be utilized in the methods provided herein. For example, arrays can be on a solid substrate (a solid phase array), such as a glass slide, or on a semi-solid substrate, such as nitrocellulose membrane. Arrays can also be presented on beads, i.e., a bead array. These beads are typically microscopic and may be made of, e.g., polystyrene. The array can also be presented on nanoparticles, which may be made of, e.g., particularly gold, but also silver, palladium, or platinum. See, e.g., Nanosphere Verigene® System, which uses gold nanoparticle probe technology. Magnetic nanoparticles may also be used. Other examples include nuclear magnetic resonance microcoils. The nucleotide sequences can be DNA, RNA, or any permutations thereof (e.g., nucleotide analogues, such as locked nucleic acids (LNAs), and the like). In some embodiments, the nucleotide sequences span exon/intron boundaries to detect gene expression of spliced or mature RNA species rather than genomic DNA. The nucleotide sequences can also be partial sequences from a gene, primers, whole gene sequences, non-coding sequences, coding sequences, published sequences, known sequences, or novel sequences. The arrays may additionally comprise other compounds, such as antibodies, peptides, proteins, tissues, cells, chemicals, carbohydrates, and the like that specifically bind proteins or metabolites.

An array platform includes, for example, the TaqMan® Low Density Array (TLDA) mentioned above, and an Affymetrix® microarray platform.

A hybridization and multi-signal coded detector platform includes, for example, NanoString nCounter® technology, in which hybridization of a color-coded barcode attached to a target-specific probe (e.g., corresponding to a gene expression transcript of interest) is detected; and Luminex® xMAP® technology, in which microsphere beads are color coded and coated with a target-specific (e.g., gene expression transcript) probe for detection; and Illumina® BeadArray, in which microbeads are assembled onto fiber optic bundles or planar silica slides and coated with a target-specific (e.g., gene expression transcript) probe for detection.

A nucleic acid mass spectrometry platform includes, for example, the Ibis Biosciences Plex-ID® Detector, in which DNA mass spectrometry is used to detect amplified DNA using mass profiles.

A thermal cycler platform includes, for example, the FilmArray® multiplex PCR system, which extract and purifies nucleic acids from an unprocessed sample and performs nested multiplex PCR; the RainDrop Digital PCR System, which is a droplet-based PCR platform using microfluidic chips; and the GenMark eSensor or ePlex systems.

The term "genetic material" refers to a material used to store genetic information in the nuclei or mitochondria of an organism's cells. Examples of genetic material include, but are not limited to, double-stranded and single-stranded DNA, cDNA, RNA, and mRNA.

The term "plurality of nucleic acid oligomers" refers to two or more nucleic acid oligomers, which can be DNA or RNA.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

As used herein, the term "subject" refers to a mammal, preferably a human. The mammals include, but are not limited to, humans, primates, livestock, rodents, and pets. A subject may be waiting for medical care or treatment, may be under medical care or treatment, or may have received medical care or treatment.

As used herein, the term "healthy control group," "normal group" or a sample from a "healthy" subject means a subject, or group subjects, who is/are diagnosed by a physician as not suffering from central nervous system tumor, or a clinical disease associated with central nervous system tumor based on qualitative or quantitative test results. A "normal" subject is usually about the same age as the individual to be evaluated, including, but not limited, subjects of the same age and subjects within a range of 5 to 10 years.

The methods provided herein are useful for interrogating a genomic region of interest as described above. It will also be readily obvious to one of skill in the art that the term "a contiguous region of the genome or a chromosome of a mammalian cell" in the methods of this invention can be used interchangeably with a genomic region of interest as described above.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

As various changes could be made in the above-described materials and methods without departing from the scope of the invention, it is intended that all matter contained in the above description and in the examples given below, shall be interpreted as illustrative and not in a limiting sense.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1: A Novel Cas9-Targeted Long-Read Assay for Simultaneous Detection of IDH1/2 Mutations and Clinically Relevant MGMT Methylation in Fresh Biopsies of Diffuse Glioma In this Example, the use of nanopore Cas9-targeted sequencing (nCATS) was explored as a sequencing technique, capable of assessing multiple biomarkers simultaneously, as an attractive option to overcome current clinical practice limitations in the detection of central nervous system tumors.

To diagnose diffuse gliomas (DG), the presence of isocitrate dehydrogenase 1 and 2 (IDH1/2) gene mutation is required for subtype identification and is also a prognostic molecular marker [Louis D N, et al. Acta Neuropathol. 2016; 131:803-820; Yan H, et al (2009) N Engl J Med 360:765-773]. The methylation status of the 06-methylguanine-DNA methyltransferase (MGMT) promoter is used routinely to guide chemotherapeutic treatment decisions, especially in glioblastoma (GBM) (e.g., grade IV astrocytoma), which is the most common type of DG.

Various methods can be used to screen for IDH1/2 mutation and MGMT promoter methylation. Typically, IDH1/2 mutation screening is performed with an immunohistochemistry (IHC) assay specific for the most common mutation at IDH1 arginine 132 (arginine to histidine, R132H). However, IHC cannot detect other less common mutations, including IDH1 R132S, R132C, R132G, and R132L substitutions or IDH2 R172K. Polymerase chain reaction (PCR) or Sanger sequencing is thus recommended as a second-step test for IHC-negative tumors [Louis D N, et al. Acta Neuropathol. 2016; 131:803-820; Capper D, et al (2010) Brain Pathol 20:245-254].

Assaying MGMT methylation requires identifying the modification of cytosine residues on CpG islands (CpG methylation) in the promoter, which includes 98 CpG dinucleotides surrounding the transcription start site. These assays vary in the methodology used and the promoter region assessed. However, most interrogate only a fraction of the CpG sites to predict the transcriptional activity of the MGMT gene and in turn to predict potential therapeutic response to temozolomide (TMZ), an oral chemotherapy drug. Two differentially methylated regions (DMRs) cover CpGs 25-50 (DMR1) and CpGs 73-90 (DMR2) and have been demonstrated to correlate with transcriptional silencing [Bienkowski M, et al (2015) Clin Neuropathol 34:250-257]. DMR2 has some cis-acting sites that control the transcription of MGMT in a cell-based reporter study [Malley D S et al., (2011) Acta Neuropathol 121:651-661]. The presence of MGMT promoter methylation portends responsiveness to TMZ treatment [Malmström A, et al (2012) Lancet Oncol 13:916-926; Wick W, et al (2012) Lancet Oncol 13:707-715], but the degree of methylation corresponding to TMZ treatment response is a subject of debate, and there is no consensus on which assay method is optimal. Commonly used methods such as methylation-specific PCR, pyrosequencing, and mass spectrometry (MassARRAY®) introduce PCR bias and are restricted to study limited sequence length due to bisulfite treatment.

Nanopore technology (Oxford Nanopore Technologies® or ONT) could overcome the limitations of the aforementioned assays to assess both methylation and mutations. Quantitative methylation assessment without bisulfite conversion is possible with nanopore sequencing, as electrolytic current signals are sensitive to methylation of carbon 5 in cytosine (5mC) [Simpson J T et al. (2017) Nat Methods 14:407-410]. In addition, with the capacity for long-read single-molecule sequencing, multiple CpGs in the promoter region and additional surrounding regions can be captured. Here, nanopore Cas9-targeted sequencing (nCATS) was applied [Gilpatrick T, et al (2020) Nat Biotechnol:1-6] and the low-cost nanopore MinION device (ONT) used to simultaneously assay IDH mutations and MGMT methylation. The results obtained were then compared against currently used clinical tests. A positive correlation between the methylation of all captured CpGs and gene expression levels was observed and showed that both nCATS and existing deep sequencing methods detected the same single nucleotide variants in clinical DG samples.

Methods

Informed consent. This study included 8 patients diagnosed with glioma. Case records were reviewed, and brain tissue samples were obtained under the approval of the institutional review board at the University of Arkansas for Medical Sciences (IRB protocol #228443). All patients provided written informed consent. Four samples with IDH mutations and 4 with IDH wild type were selected by A.R. However, all samples were processed and analyzed in a single-blind fashion before mutational status was disclosed to the analytical group (T.W. and P.J.).

DNA samples and DNA extraction for nCATS—Control DNA. IDH1/2 wild type gDNA (genomic DNA) standards (Horizon Discovery, USA) were used as the negative control for genotyping by PCR and nanopore sequencing (ONT, USA). For positive controls, IDH1 codon 132 mutant DNA (CGT→GGT) was obtained from a patient in this study; IDH2 codon 172 mutant DNA (AGG→AAG) was purchased from Horizon Discovery. Exon 4 of IDH1/2 of each standard was amplified using specific primers (Integrated DNA Technologies, USA). PCR conditions for IDH1/2 amplifications were identical, using 100 ng gDNA, 20 mM primers, and 25 μl LongAmp Taq 2× Master Mix (NEB, USA) with the following program: 95° C. 2 min, 25 cycles of [95° C. 15 s, 60° C. 30 s, 65° C. 40 s], 65° C. 10 min, 4° C. hold. PCR reactions were purified with AMPure XP beads (Beckman Coulter, USA) and eluted in 20 μl nuclease-free water (NEB). The purified PCR products were used for library preparation using 1D Native barcoding genomic DNA with EXP-NBD103 and SQK-LSK108 protocols (ONT) and nanopore sequencing with the R9.4.1/FLO-MIN106 flow cell (ONT).

The CpGenome™ DNA Standard Set (MilliporeSigma, USA) containing 5-mC and unmodified cytosines was used for quantitative analysis. The standard DNAs consist of linear, double-stranded DNA (897 bp) with 52 CpG sites; each standard contains either 100% 5-mCs or unmodified cytosines.

The CpGenome™ Human Methylated & Non-Methylated DNA Standard Set (MilliporeSigma) was used as the positive and negative control for nCATS and methylation status assessment. The Methylated DNA Standard is methylated enzymatically at all CpG dinucleotides (>95%). The Non-Methylated DNA Standard contains less than 5% methylated DNA.

Cell line gDNA. Four GBM cell lines were used in this study: U87, U251, T98G, and LN18 (Sigma, USA). The cells were grown to 85-90% confluence in 10-cm dishes in DMEM (U87) with 10% fetal bovine serum (FBS); EMEM (U251 and T98G) with 2 mM glutamine, 1% NEAA, 1 mM sodium pyruvate, and 10% FBS; and in DMEM (LN18) with 5% FBS utilizing standard techniques. The cells were washed with PBS before DNA extraction with the AllPrep® DNA/RNA Mini Kit (Qiagen, USA). Eluted gDNA was purified and concentrated using AMPure™ XP beads and eluted in 20-40 μl nuclease-free water and stored at −20° C.

Clinical samples. The study included 8 brain tissue samples graded according to the 2016 WHO classification for diffuse glioma by a board-certified neuropathologist, Murat Gokden M. D. (Table 1). Following surgical resection, tissue samples were immediately frozen on dry ice and stored at −80° C. until DNA extraction. DNA extraction was carried out with the AllPrep@ DNA/RNA Mini Kit (Qiagen) as described above.

RNA extraction. For all cell lines and tissue samples, RNA and DNA were extracted from the same samples. The AllPrep DNA/RNA Mini Kit (Qiagen) allows the simultaneous purification of gDNA and total RNA from the same sample.

TABLE 1

Demographic characteristics of 8 patients

| Patient ID | P553 | P690 | P701 | P568 | P785 | P712 | P816 | P722 |
|---|---|---|---|---|---|---|---|---|
| Age | 29 | 24 | 57 | 42 | 72 | 37 | 48 | 73 |
| Gender | Male | Male | Male | Male | Female | Female | Female | Female |
| Race | White | White | White | White | White | White | White | White |
| Pathology Diagnosis | Secondary GBM, WHO Grade 4 | Secondary GBM, WHO Grade 4 | Diffuse astrocytoma, WHO Grade 2 | Diffuse astrocytoma, WHO Grade 2 | Anaplastic astrocytoma, WHO Grade 3 | Anaplastic astrocytoma, WHO Grade 3 | GBM, WHO Grade 4 | GBM, WHO Grade 4 |
| MGMT Status | Low level detected | Detected | Detected | Detected | Not detected | Detected | Detected | Detected |
| IDH | Mutant | Mutant | Mutant | Mutant | Not detected | Not detected | Not detected | Not detected |
| Previous Chemo | Yes | Yes | No | No | No | No | No | No |
| Chemo Agent | TMZ | TMZ | NA | NA | NA | NA | NA | NA |
| Previous Radiation | Yes | Yes | No | No | No | No | No | No |
| Previous Radiation Dose | 50.4Gy | 60Gy | NA | NA | NA | NA | NA | NA |
| Previous Diagnosis | Diffuse astrocytoma, WHO Grade 2 | Oligoastrocytoma, WHO Grade 2 | NA | NA | NA | NA | NA | NA |
| Progression Interval (months) | 30 | 55 | NA | NA | NA | NA | NA | NA |
| Vital Status | Alive | Alive | Alive | Alive | Alive | Alive | Deceased | Deceased |

Purity, quantity, and integrity of DNA and RNA. DNA and RNA purity was assessed in all samples with a NanoDrop™-2000 spectrophotometer (Thermo Scientific, USA). DNA concentration was measured using a Qubit® 3.0 quantification assay (Thermo Scientific). The integrity of DNA and RNA was determined using a TapeStation 2200 (Agilent, USA).

Single guide (sg)RNA design. To design the crRNAs, we used CHOPCHOP as described in the ONT protocol [Labun K, et al., (2019) Nucleic Acids Res 47:W171-W174]. The specificity of the crRNA was tested with the UCSC In-Silico PCR tool to search against the human genome (hg19). The designed crRNAs, tracrRNA, and HiFi Cas9 were purchased from IDT. The following crRNAs were used:

```
MGMT_promoter_left:
                                   (SEQ ID NO: 1)
ATGAGGGGCCCACTAATTGA;

MGMT_promoter_right:
                                   (SEQ ID NO: 2)
ACCTGAGTATAGCTCCGTAC;

IDH1_left:
                                   (SEQ ID NO: 3)
ACAGTCCATGAATCAACCTG;

IDH1_right:
                                   (SEQ ID NO: 4)
GGCACCATACGAAATATTCT;

IDH2_left:
                                   (SEQ ID NO: 5)
GCTAGGCGAGGAGCTCCAGT;

IDH2_right:
                                   (SEQ ID NO: 6)
GCTGTTGGGGCCGCTCTCGA.
```

nCATS library preparation for targeted sequencing by ONT. For each sample, 3.5 μg to 5.5 μg gDNA was used as input for preparing the nCATS library. The library preparation protocol was provided by ONT via the Enrichment Channel, Nanopore Community (protocol version: ENR9084_v109_revA4dec.2018). Briefly, gDNA ends were treated with calf intestinal phosphatase (NEB) to reduce the ligation of sequencing adapters to non-target strands. Then, Cas9 ribonucleoprotein complexes (Cas9 RNPs) were freshly prepared and used for generating double-strand breaks at targeted regions of blocked DNA. An adenine (A)-tail was immediately added to the 3' ends of cut DNA fragments using Taq polymerase and dATP (NEB). The A overhang can pair with the T overhang of nanopore sequencing adapters. Both adapter-ligated DNA and blocked DNA were added to the flow cell for sequencing. The excess unligated adapters were removed with AMPure XP beads (Beckman Coulter). The library (molecules ligated to the adapters) were sequenced with the MinION Mk1B. Each library was sequenced for 36 hon an R9.4.1/FLO-MIN106 flow cell (ONT).

Bioinformatics and statistical analysis—Data processing and mapping of reads: The ONT raw signal data (FAST5 files) generated by MinKnow software (version 1.7.14) were converted to DNA (FASTQ files) using the GUPPY algorithm (version 3.0.3). Quality control for ONT reads were performed to filter FASTQ files based on a mean quality threshold higher than Phred score 8 and read lengths longer than 200 bases using NanoFilt program [PMID: 29547981]. We aligned the filtered reads to the human reference genome (Hg19) using Minimap2 and sorted with SAMtools (version 1.6).

Command-Lines:

```
guppy_basecaller --recursive --enable_trimming true --qscore_filtering -- min_qscore 8 --kit SQK-LSK109 --flowcell FLO-MIN106 --input_path fast5_dir --save_path fastq_dir
cat fastq_dir/pass/*.fastq|NanoFilt -I 200>reads.fastq
minimap2 -ax map-ont hgl9.genome.fasta reads.fastq|samtools sort -T tmp -o reads.mappings.bam
samtools index reads.mappings.bam
```

Nanopore methylation calling: CpG methylation (5mC) calling was performed using Nanopolish v 0.11.0 9 using the reads (FASTQ files), aligned reads (BAM files), and raw signal (FAST5 files) for each sample. We then calculated the methylation frequency and log-likelihood ratios of methylation at each position using "calculate_methylation_frequency.py" from Nanopolish package. We filtered out any position with <10 reads and log-likelihood ratios of <2.5 in each sample.

Command-Lines:

```
nanopolish index -d fast5_dir/reads.fastq
nanopolish call-methylation -r reads.fastq -b reads.mappings.bam -g
hg19.genome.fasta>methylation_calls.tsv
calculate_methylation_frequency.py methylation_calls.tsv|awk
'BEGIN{OFS="\t"}{if($5>=10) print $1,$2,$3, $7}'>methylation_calls.bdg
```

Single-nucleotide variant calling: SNVs were called over the target regions with Nanopolish using FASTQ files, BAM files, and FAST5 files. Nanopolish was used to reanalyze the raw signals after alignment and to calculate SNV allele frequencies from the ONT data at the signal level. The "nanopolish variants" subprogram was used to simultaneously call SNVs with a modified parameter setting: -min-candidate-frequency=0.15, -min-candidate-depth=10, --methylation-aware=cpg, --snps, and --ploidy=2. We reviewed the variant quality of SNVs and visualized them with the Integrative Genomics Viewer and trackViewer [Ou J, et al., Nat Methods. 16(6):453-454, 22; Robinson J T, et al., (2011) Nat Biotechnol. 29(1):24-26].

```
Command-lines:
declare -a regions=( \
  'chr10:131264610-131266825' \
  'chr2:209111275-209113183' \
  'chr15:90631754-90633046' \
  )
for locus in ${regions[@]}; do
  nanopolish variants -min-candidate-depth 10 -min-candidate-frequency 0.15 \
    --methylation-aware=cpg --snps -r reads.fastq -b reads.mappings.bam \
    -g hg19.genome.fasta --ploidy=2 -w $locus > snv_${locus}__variants.vcf
```

-continued

```
    bgzip snv__${locus}__variants.vcf
    bcftools index snv__${locus}__variants.vcf.gz
done
bcftools concat snv__*__variants.vcf.gz -o snv__*__variants.combine.vcf
```

MGMT gene expression analysis with quantitative reverse transcriptase (qRT)-PCR. A total of 1 µg extracted RNA was reverse transcribed to eDNA using SuperScript™IV reverse transcriptase (Invitrogen, USA). qRT-PCR analysis was performed using iTaq™ Universal SYBR& Green Supermix (BioRad, USA) and the StepOnePlus™ Real-Time PCR System (Applied Biosystems, USA). Real-time PCR was carried out in technical triplicates; it was run at 95° C. for 10 min, at 40 cycles of 95° C. for 15 s, and at 60° C. for 60 s. A published primer set was used for MGMT and the 8-actin gene (ACTB) [Cartularo L, et al., (2016) PLOS One 11: e0155002; Chen X, et al., (2018) Nat Commun 9:2949; Uno M, et al., (2011) Clinics 66:1747-1755]. For data analysis, the average result in each triplicate was used.

Illumina™ sequencing of patient tumor samples. DNA and RNA sequencing was performed on clinical tumor specimens and saliva samples (from the same patients as the tumor specimens) for 6 of the 8 patients using the Tempus xT™ assay [Beaubier N, et al., (2019) Nat Biotechnol 37:1351-1360]. Briefly, nucleic acid was extracted from tumor tissue sections with tumor cellularity greater than 20% using a Chemagic™ 360 instrument and a source-specific magnetic bead protocol. Total nucleic acid was used for DNA library construction, while RNA was further purified by DNase I digestion and magnetic bead purification. The nucleic acid was quantified with a Quant-i™ PicoGreen™ dsDNA Kit or Quant-i™ RiboGreen™ RNA Kit (Life Technologies), and quality was confirmed with a LabChip® GX Touch™ HT Genomic DNA Reagent Kit or LabChip® RNA High HT Pico Sensitivity Reagent Kit (PerkinElmer).

For DNA library construction, 100 ng DNA from tumor or normal samples was mechanically sheared to an average size of 200 bp using a Covaris ultrasonicator. The libraries were prepared using the KAPA Hyper Prep Kit. Briefly, DNA underwent enzymatic end repair and A-tailing, followed by adapter ligation, bead-based size selection, and PCR. The captured DNA targets were amplified using the KAPA HiFi™ HotStart ReadyMix. The amplified target-captured libraries were sequenced on an Illumina™ HiSeq® 4000 System with patterned flow cell technology.

Results (i) Nanopore Sequencing Accurately Assesses Mutational Status and Methylation Levels The error rate of raw nanopore sequencing reads continues to decrease, allowing the technology to be used for genotyping and methylation assays [Simpson J T, et al., (2017) Nat Methods 14:407-410]. Nanopore sequencing errors are largely random and use of a consensus sequence from sufficient read depth can eliminate almost all of the sequencing error. To confirm the ability of nanopore sequencing to accurately genotype the IDH mutations, PCR amplicons were sequenced that were IDH1/2 wild type or IDH1/2 mutant using a nanopore MinION device. This test showed that heterozygous mutations in these 2 genes could be accurately detected, although artificial errors are inevitable (FIG. 1A).

Figure 1B:
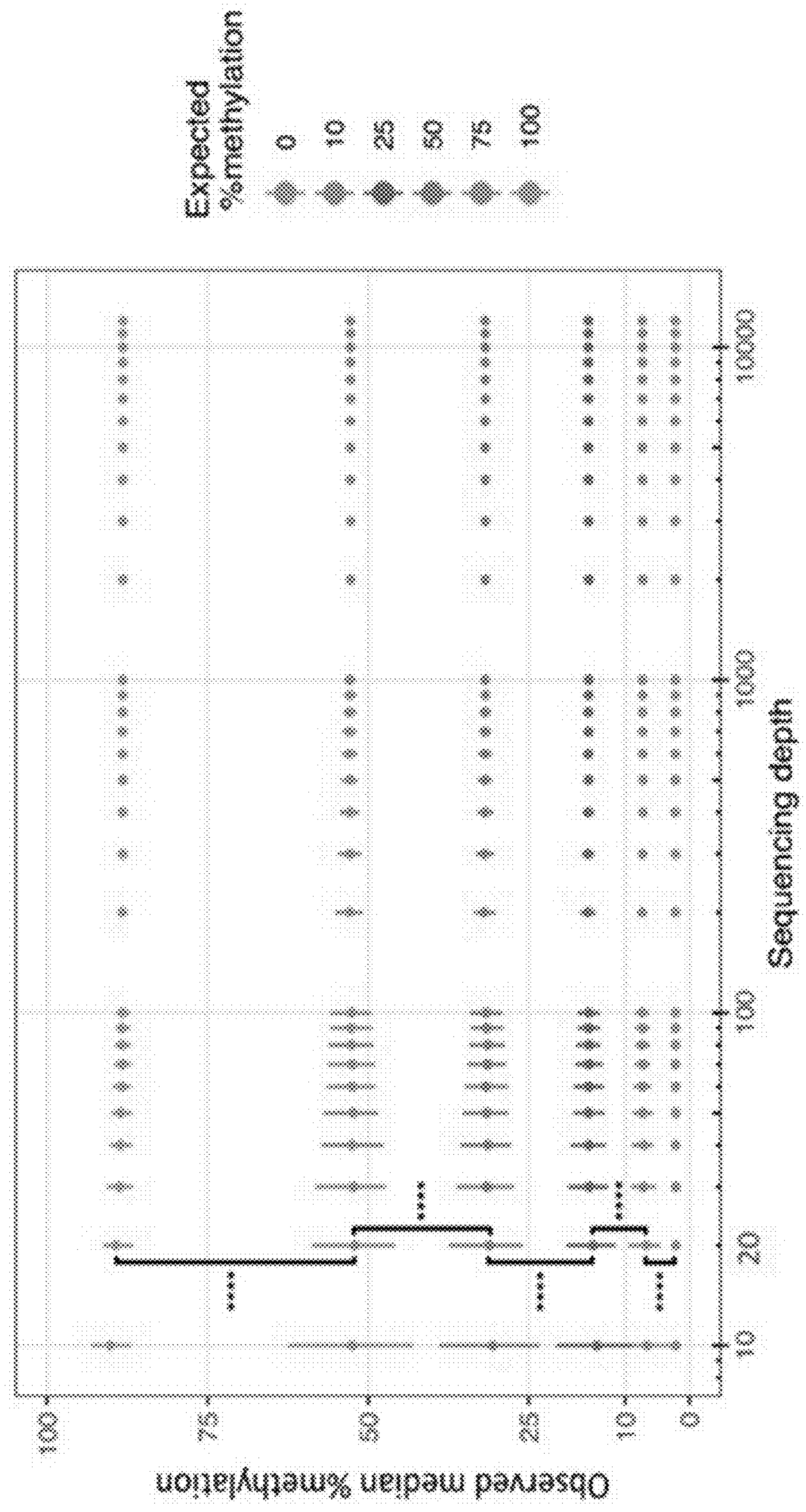

To determine the limit of detection for CpG methylation, 2 synthetic DNA standards were sequenced with that were either 100% methylated or 0% methylated on CpGs and then used Nanopolish for methylation calling [Simpson J T, et al., (2017) Nat Methods 14:407-410]. Data for 10%, 25%, 50%, or 75% methylated CpGs were generated by randomly sampling the reads from the 0 and 100% methylated standards. It was found that at a low sequencing coverage of ~10 reads (10×), methylation could be measured, but with high variation. Decreasing of coefficient of variation when increasing of sequencing depth was observed. At higher depth, 20×, the standard deviation was lower (FIG. 1B), and methylation levels of 0%, 25%, 50%, 75%, and 100% could be distinguished. Thus, 20× was used as the theoretical limit of detection in this Example.

(ii) nCATS MGMT Methylation Assay is Comparable to Pyrosequencing Assays

Figure 1C:
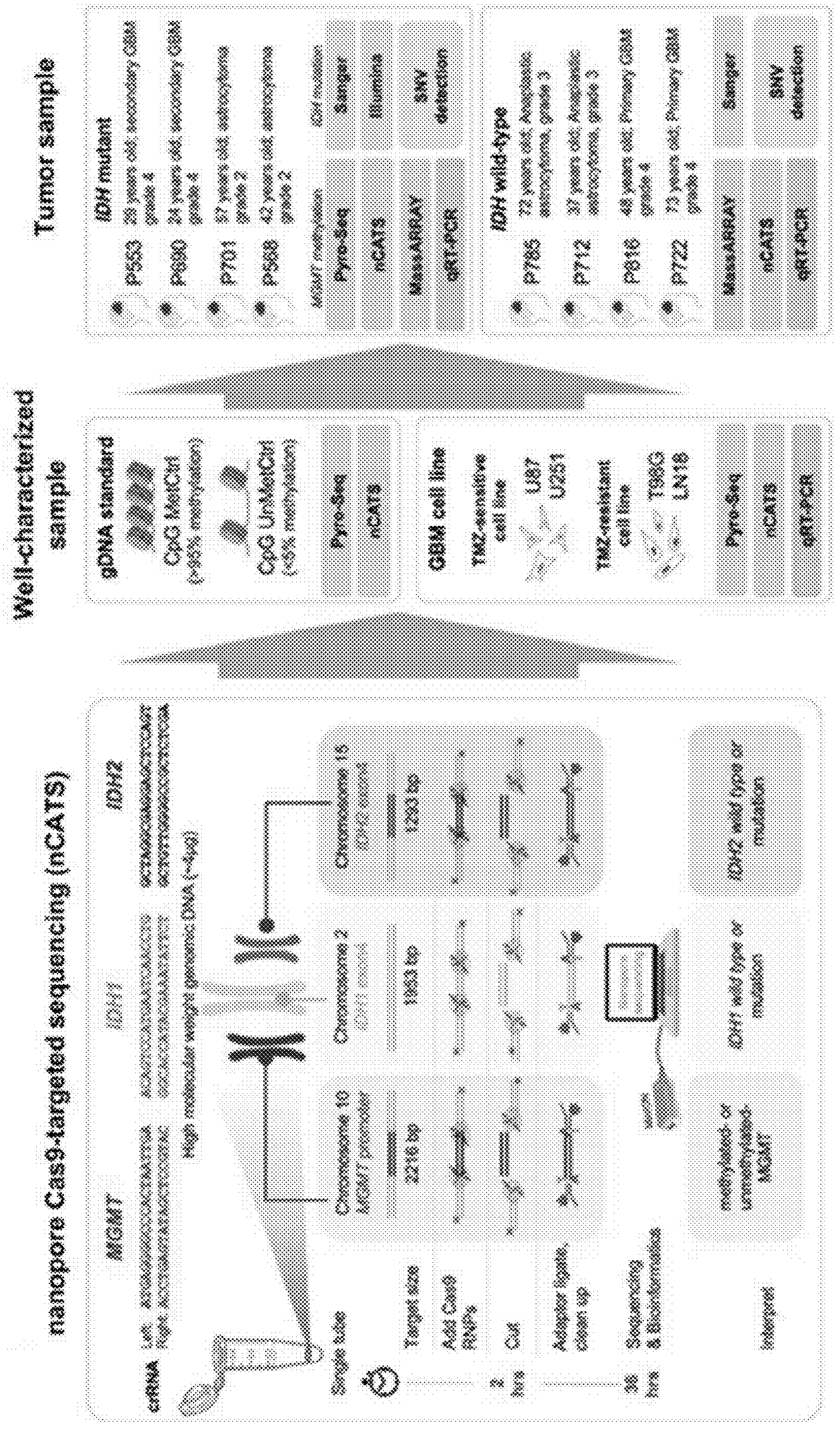
Figure 1D:
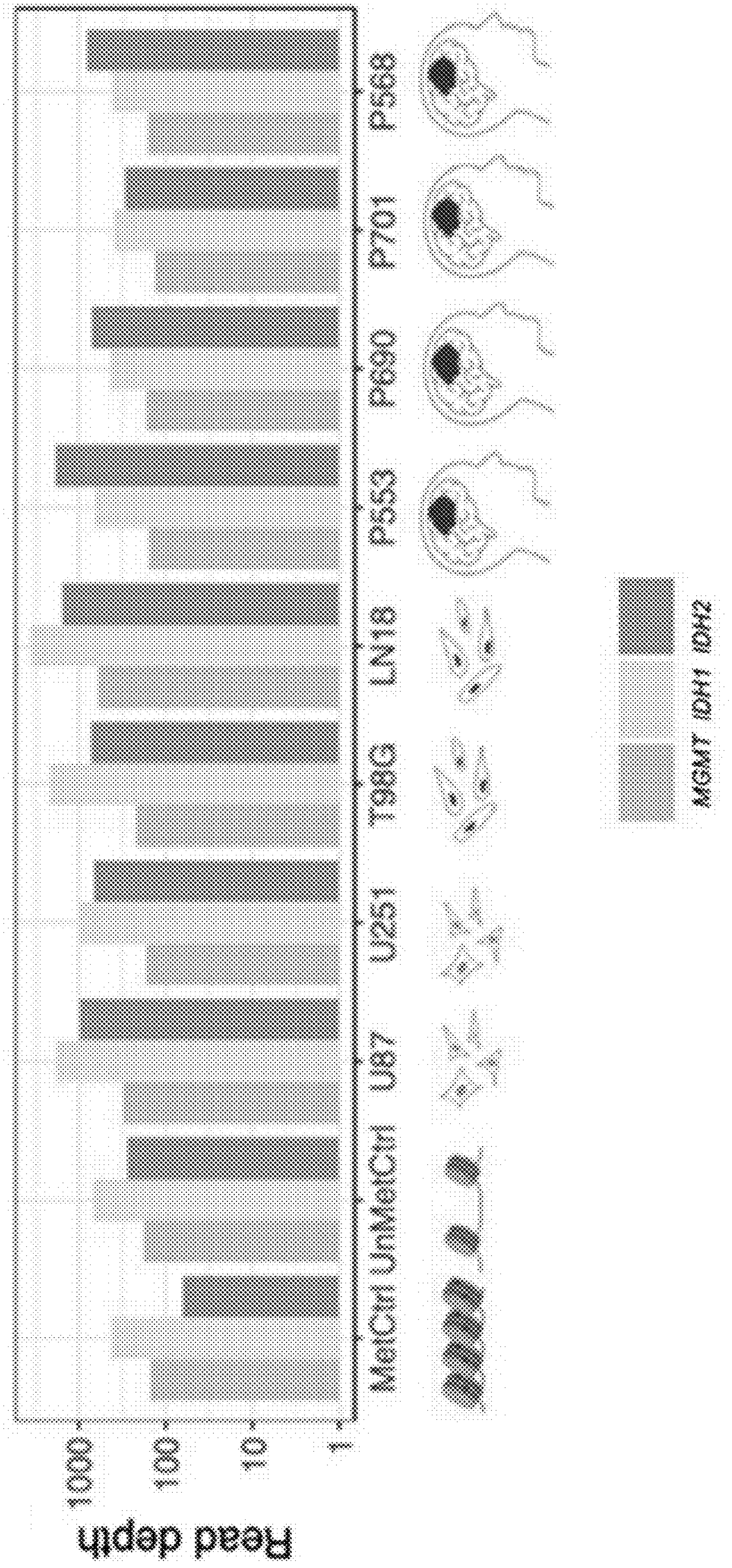
Figure 2A:
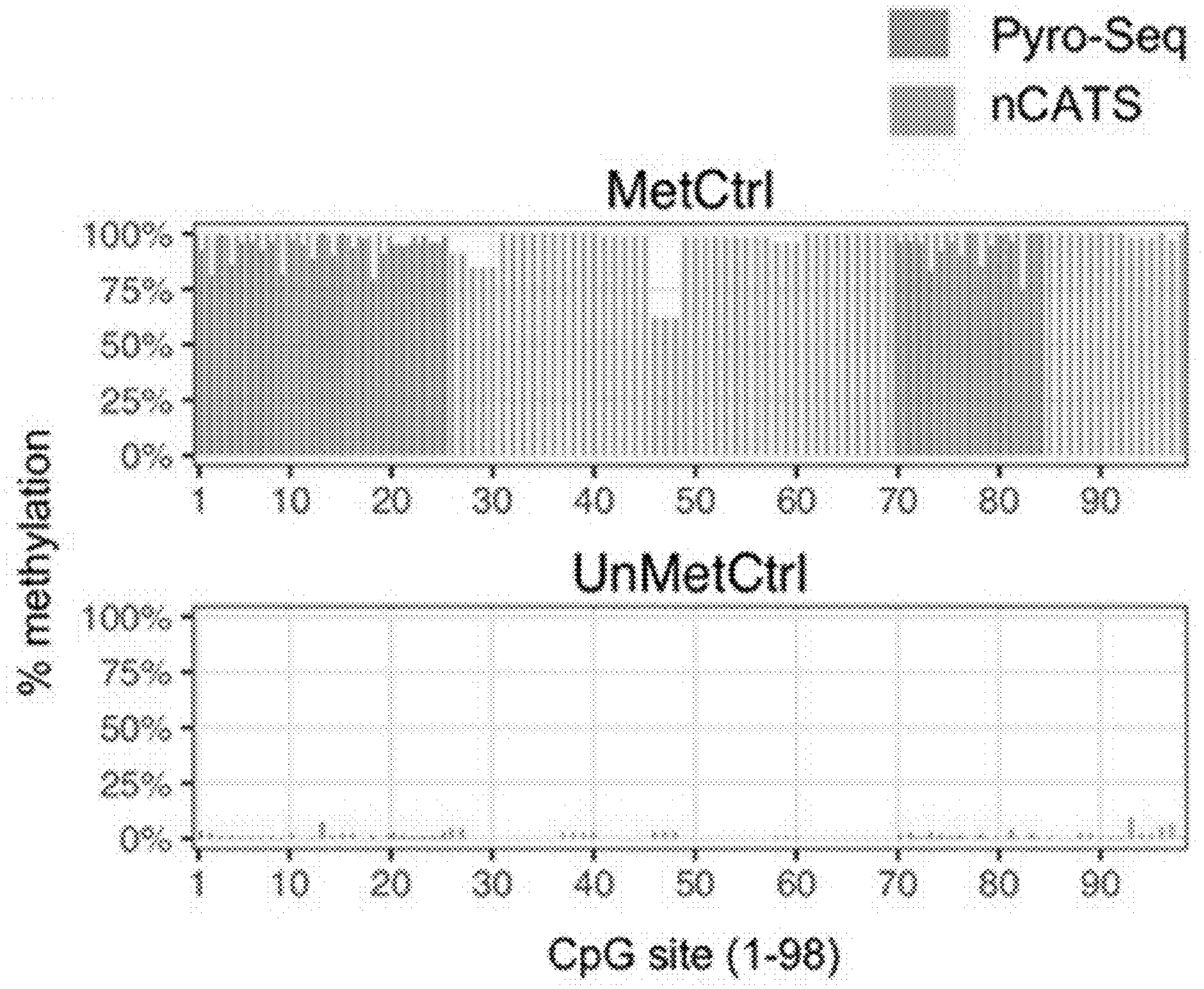
FIG. 2A-2D show simultaneous assessment of MGMT and IDH status in 4 IDH-mutant clinical samples.

Based on these preliminary data, guide RNA for the nanopore Cas9-targeted sequencing (nCATS) workflow were then designed to test on 4 human GBM cell lines (2 TMZ-sensitive [U87 and U251]) and 2 TMZ-resistant [T98G and LN18] and 8 clinical DG samples (4 IDH mutant and 4 IDH wild type) (FIG. 1C and Table 1). Sequencing depth coverage was an average of 184, 664, and 939 for MGMT, IDH1, and IDH2, respectively (FIG. 1D).

nCATS was then used to perform targeted sequencing of the MGMT gene; this approach captured 98 CpGs (located in promoter and exon 1) and 121 CpGs (in a 5'end of intron 1). The genomic coordinates of CpG loci are shown in Table 2. The first 98 CpGs have been studied by others, and a subset of CpGs in this region has been used clinically to assess methylation [Mansouri A, et al (2018) MGMT promoter methylation status testing to guide therapy for glioblastoma: refining the approach based on emerging evidence and current challenges. Neuro Oncol]. Thus, the 98 CpGs were first focused on and used them to compare the methylation levels obtained by nCATS to levels obtained by pyrosequencing assays. Using a methylated and unmethylated DNA standard with >95% vs<5% methylation, respectively, nCATS provided a clear methylation pattern in both samples (FIG. 2A) that was comparable to the results of bisulfite modification-PCR-pyrosequencing for CpGs 1-25 and 70-84.

TABLE 2

Location of each CpGs captured by nCATS

| Chromosome # | Chromosome location (bp) | | CpG # |
|---|---|---|---|
| chr10 | 131264955 | 131264955 | 1 |
| chr10 | 131264964 | 131264964 | 2 |
| chr10 | 131264970 | 131264970 | 3 |
| chr10 | 131264975 | 131264975 | 4 |
| chr10 | 131264985 | 131264985 | 5 |
| chr10 | 131265001 | 131265001 | 6 |
| chr10 | 131265005 | 131265005 | 7 |
| chr10 | 131265008 | 131265008 | 8 |
| chr10 | 131265015 | 131265015 | 9 |
| chr10 | 131265022 | 131265022 | 10 |
| chr10 | 131265024 | 131265024 | 11 |

TABLE 2-continued

| Location of each CpGs captured by nCATS | | | |
|---|---|---|---|
| Chromosome # | Chromosome location (bp) | | CpG # |
| chr10 | 131265026 | 131265026 | 12 |
| chr10 | 131265042 | 131265042 | 13 |
| chr10 | 131265048 | 131265048 | 14 |
| chr10 | 131265058 | 131265058 | 15 |
| chr10 | 131265066 | 131265066 | 16 |
| chr10 | 131265070 | 131265070 | 17 |
| chr10 | 131265072 | 131265072 | 18 |
| chr10 | 131265100 | 131265100 | 19 |
| chr10 | 131265136 | 131265136 | 20 |
| chr10 | 131265151 | 131265151 | 21 |
| chr10 | 131265154 | 131265154 | 22 |
| chr10 | 131265158 | 131265158 | 23 |
| chr10 | 131265168 | 131265168 | 24 |
| chr10 | 131265172 | 131265172 | 25 |
| chr10 | 131265184 | 131265184 | 26 |
| chr10 | 131265193 | 131265193 | 27 |
| chr10 | 131265205 | 131265205 | 28 |
| chr10 | 131265208 | 131265208 | 29 |
| chr10 | 131265214 | 131265214 | 30 |
| chr10 | 131265228 | 131265228 | 31 |
| chr10 | 131265231 | 131265231 | 32 |
| chr10 | 131265236 | 131265236 | 33 |
| chr10 | 131265239 | 131265239 | 34 |
| chr10 | 131265246 | 131265246 | 35 |
| chr10 | 131265254 | 131265254 | 36 |
| chr10 | 131265272 | 131265272 | 37 |
| chr10 | 131265275 | 131265275 | 38 |
| chr10 | 131265278 | 131265278 | 39 |
| chr10 | 131265281 | 131265281 | 40 |
| chr10 | 131265294 | 131265294 | 41 |
| chr10 | 131265297 | 131265297 | 42 |
| chr10 | 131265302 | 131265302 | 43 |
| chr10 | 131265306 | 131265306 | 44 |
| chr10 | 131265310 | 131265310 | 45 |
| chr10 | 131265321 | 131265321 | 46 |
| chr10 | 131265330 | 131265330 | 47 |
| chr10 | 131265337 | 131265337 | 48 |
| chr10 | 131265348 | 131265348 | 49 |
| chr10 | 131265354 | 131265354 | 50 |
| chr10 | 131265356 | 131265356 | 51 |
| chr10 | 131265358 | 131265358 | 52 |
| chr10 | 131265363 | 131265363 | 53 |
| chr10 | 131265369 | 131265369 | 54 |
| chr10 | 131265375 | 131265375 | 55 |
| chr10 | 131265377 | 131265377 | 56 |
| chr10 | 131265379 | 131265379 | 57 |
| chr10 | 131265404 | 131265404 | 58 |
| chr10 | 131265410 | 131265410 | 59 |
| chr10 | 131265415 | 131265415 | 60 |
| chr10 | 131265427 | 131265427 | 61 |
| chr10 | 131265434 | 131265434 | 62 |
| chr10 | 131265437 | 131265437 | 63 |
| chr10 | 131265446 | 131265446 | 64 |
| chr10 | 131265455 | 131265455 | 65 |
| chr10 | 131265461 | 131265461 | 66 |
| chr10 | 131265467 | 131265467 | 67 |
| chr10 | 131265469 | 131265469 | 68 |
| chr10 | 131265474 | 131265474 | 69 |
| chr10 | 131265493 | 131265493 | 70 |
| chr10 | 131265495 | 131265495 | 71 |
| chr10 | 131265506 | 131265506 | 72 |
| chr10 | 131265513 | 131265513 | 73 |
| chr10 | 131265518 | 131265518 | 74 |
| chr10 | 131265521 | 131265521 | 75 |
| chr10 | 131265525 | 131265525 | 76 |
| chr10 | 131265535 | 131265535 | 77 |
| chr10 | 131265537 | 131265537 | 78 |
| chr10 | 131265542 | 131265542 | 79 |
| chr10 | 131265547 | 131265547 | 80 |
| chr10 | 131265553 | 131265553 | 81 |
| chr10 | 131265574 | 131265574 | 82 |
| chr10 | 131265579 | 131265579 | 83 |
| chr10 | 131265585 | 131265585 | 84 |
| chr10 | 131265595 | 131265595 | 85 |
| chr10 | 131265608 | 131265608 | 86 |
| chr10 | 131265613 | 131265613 | 87 |

TABLE 2-continued

| Location of each CpGs captured by nCATS | | | |
|---|---|---|---|
| Chromosome # | Chromosome location (bp) | | CpG # |
| chr10 | 131265625 | 131265625 | 88 |
| chr10 | 131265641 | 131265641 | 89 |
| chr10 | 131265652 | 131265652 | 90 |
| chr10 | 131265655 | 131265655 | 91 |
| chr10 | 131265658 | 131265658 | 92 |
| chr10 | 131265670 | 131265670 | 93 |
| chr10 | 131265691 | 131265691 | 94 |
| chr10 | 131265695 | 131265695 | 95 |
| chr10 | 131265708 | 131265708 | 96 |
| chr10 | 131265746 | 131265746 | 97 |
| chr10 | 131265773 | 131265773 | 98 |
| chr10 | 131265795 | 131265795 | 99 |
| chr10 | 131265802 | 131265802 | 100 |
| chr10 | 131265809 | 131265809 | 101 |
| chr10 | 131265851 | 131265851 | 102 |
| chr10 | 131265858 | 131265858 | 103 |
| chr10 | 131265897 | 131265897 | 104 |
| chr10 | 131265932 | 131265932 | 105 |
| chr10 | 131265934 | 131265934 | 106 |
| chr10 | 131266093 | 131266093 | 107 |
| chr10 | 131266120 | 131266120 | 108 |
| chr10 | 131266128 | 131266128 | 109 |
| chr10 | 131266140 | 131266140 | 110 |
| chr10 | 131266167 | 131266167 | 111 |
| chr10 | 131266317 | 131266317 | 112 |
| chr10 | 131266439 | 131266439 | 113 |
| chr10 | 131266556 | 131266556 | 114 |
| chr10 | 131266596 | 131266596 | 115 |
| chr10 | 131266598 | 131266598 | 116 |
| chr10 | 131266628 | 131266628 | 117 |
| chr10 | 131266663 | 131266663 | 118 |
| chr10 | 131266708 | 131266708 | 119 |
| chr10 | 131266710 | 131266710 | 120 |
| chr10 | 131266738 | 131266738 | 121 |
| chr10 | 131266808 | 131266808 | 122 |
| chr10 | 131266885 | 131266885 | 123 |
| chr10 | 131266913 | 131266913 | 124 |
| chr10 | 131267008 | 131267008 | 125 |
| chr10 | 131267079 | 131267079 | 126 |
| chr10 | 131267096 | 131267096 | 127 |
| chr10 | 131267104 | 131267104 | 128 |
| chr10 | 131267126 | 131267126 | 129 |
| chr10 | 131267129 | 131267129 | 130 |
| chr10 | 131267343 | 131267343 | 131 |
| chr10 | 131267796 | 131267796 | 132 |
| chr10 | 131267865 | 131267865 | 133 |
| chr10 | 131267885 | 131267885 | 134 |
| chr10 | 131267962 | 131267962 | 135 |
| chr10 | 131268008 | 131268008 | 136 |
| chr10 | 131268072 | 131268072 | 137 |
| chr10 | 131268118 | 131268118 | 138 |
| chr10 | 131268172 | 131268172 | 139 |
| chr10 | 131268194 | 131268194 | 140 |
| chr10 | 131268276 | 131268276 | 141 |
| chr10 | 131268294 | 131268294 | 142 |
| chr10 | 131268399 | 131268399 | 143 |
| chr10 | 131268499 | 131268499 | 144 |
| chr10 | 131268681 | 131268681 | 145 |
| chr10 | 131268848 | 131268848 | 146 |
| chr10 | 131268885 | 131268885 | 147 |
| chr10 | 131268891 | 131268891 | 148 |
| chr10 | 131268920 | 131268920 | 149 |
| chr10 | 131268926 | 131268926 | 150 |
| chr10 | 131268958 | 131268958 | 151 |
| chr10 | 131268978 | 131268978 | 152 |
| chr10 | 131269075 | 131269075 | 153 |
| chr10 | 131269276 | 131269276 | 154 |
| chr10 | 131269308 | 131269308 | 155 |
| chr10 | 131269341 | 131269341 | 156 |
| chr10 | 131269360 | 131269360 | 157 |
| chr10 | 131269363 | 131269363 | 158 |
| chr10 | 131269417 | 131269417 | 159 |
| chr10 | 131269429 | 131269429 | 160 |
| chr10 | 131269468 | 131269468 | 161 |
| chr10 | 131269470 | 131269470 | 162 |
| chr10 | 131269523 | 131269523 | 163 |

TABLE 2-continued

Figure 2B:
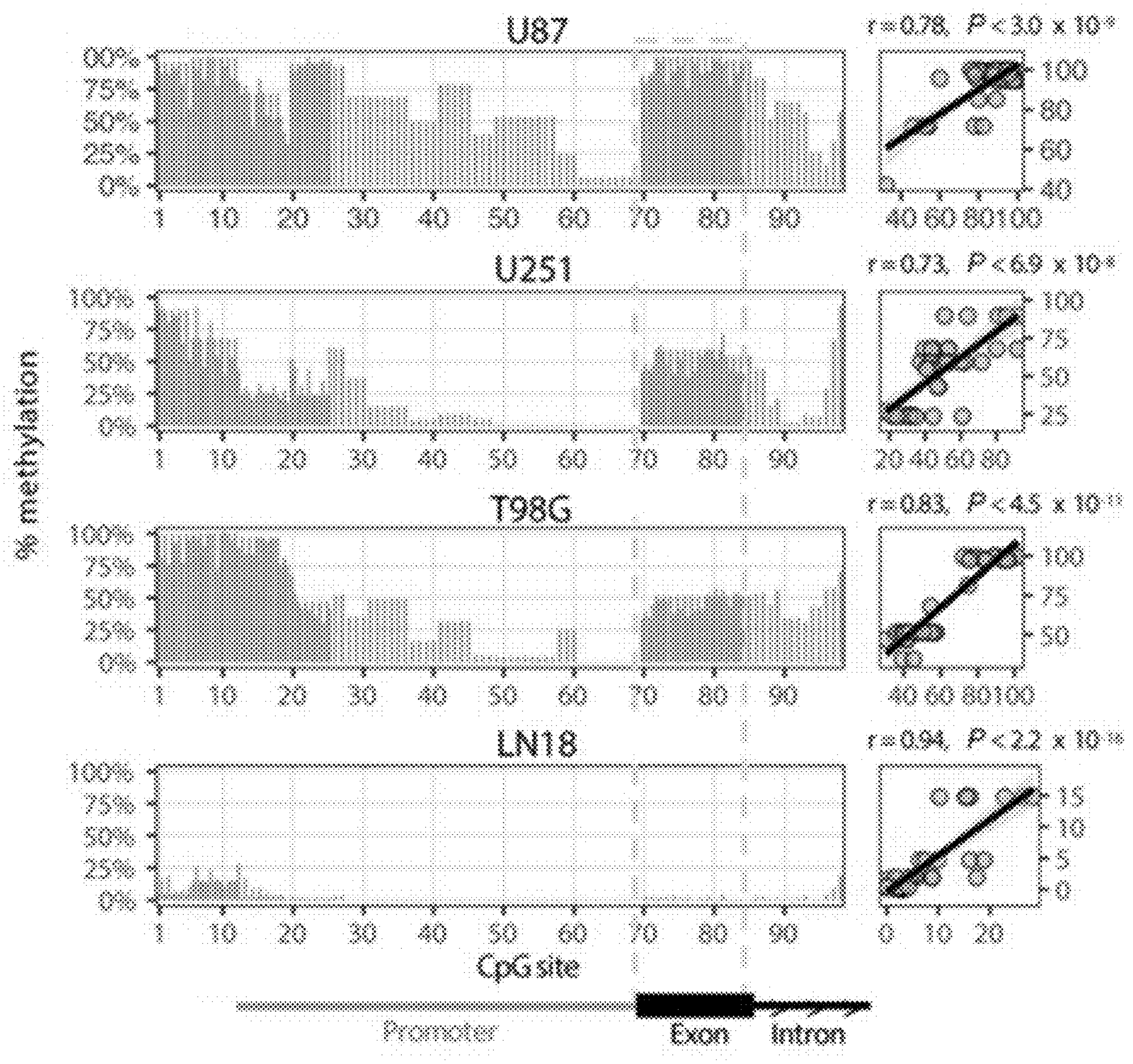

| Location of each CpGs captured by nCATS | | | |
|---|---|---|---|
| Chromosome # | Chromosome location (bp) | | CpG # |
| chr10 | 131269538 | 131269538 | 164 |
| chr10 | 131269558 | 131269558 | 165 |
| chr10 | 131269655 | 131269655 | 166 |
| chr10 | 131269720 | 131269720 | 167 |
| chr10 | 131269731 | 131269731 | 168 |
| chr10 | 131269792 | 131269792 | 169 |
| chr10 | 131269811 | 131269811 | 170 |
| chr10 | 131269842 | 131269842 | 171 |
| chr10 | 131269878 | 131269878 | 172 |
| chr10 | 131269942 | 131269942 | 173 |
| chr10 | 131270083 | 131270083 | 174 |
| chr10 | 131270109 | 131270109 | 175 |
| chr10 | 131270156 | 131270156 | 176 |
| chr10 | 131270178 | 131270178 | 177 |
| chr10 | 131270276 | 131270276 | 178 |
| chr10 | 131270295 | 131270295 | 179 |
| chr10 | 131270297 | 131270297 | 180 |
| chr10 | 131270304 | 131270304 | 181 |
| chr10 | 131270313 | 131270313 | 182 |
| chr10 | 131270478 | 131270478 | 183 |
| chr10 | 131270565 | 131270565 | 184 |
| chr10 | 131270579 | 131270579 | 185 |
| chr10 | 131270588 | 131270588 | 186 |
| chr10 | 131270606 | 131270606 | 187 |
| chr10 | 131270689 | 131270689 | 188 |
| chr10 | 131270702 | 131270702 | 189 |
| chr10 | 131270710 | 131270710 | 190 |
| chr10 | 131270713 | 131270713 | 191 |
| chr10 | 131270726 | 131270726 | 192 |
| chr10 | 131270734 | 131270734 | 193 |
| chr10 | 131270755 | 131270755 | 194 |
| chr10 | 131270811 | 131270811 | 195 |
| chr10 | 131270851 | 131270851 | 196 |
| chr10 | 131270971 | 131270971 | 197 |
| chr10 | 131270994 | 131270994 | 198 |
| chr10 | 131271007 | 131271007 | 199 |
| chr10 | 131271019 | 131271019 | 200 |
| chr10 | 131271051 | 131271051 | 201 |
| chr10 | 131271085 | 131271085 | 202 |
| chr10 | 131271223 | 131271223 | 203 |
| chr10 | 131271226 | 131271226 | 204 |
| chr10 | 131271261 | 131271261 | 205 |
| chr10 | 131271326 | 131271326 | 206 |
| chr10 | 131271385 | 131271385 | 207 |
| chr10 | 131271403 | 131271403 | 208 |
| chr10 | 131271465 | 131271465 | 209 |
| chr10 | 131271469 | 131271469 | 210 |
| chr10 | 131271496 | 131271496 | 211 |
| chr10 | 131271504 | 131271504 | 212 |
| chr10 | 131271546 | 131271546 | 213 |
| chr10 | 131271636 | 131271636 | 214 |
| chr10 | 131271643 | 131271643 | 215 |
| chr10 | 131271705 | 131271705 | 216 |
| chr10 | 131271740 | 131271740 | 217 |
| chr10 | 131271747 | 131271747 | 218 |
| chr10 | 131271868 | 131271868 | 219 |

nCATS was next applied to 4 well-characterized GBM cell lines (described above). The percent methylation of these 4 cell lines assayed by nCATS also correlated positively ($r=0.73$, $P=6.9\times10^{-8}$ to $r=0.94$, $P=2.2\times10^{-16}$) with the percent methylation returned by pyrosequencing (FIG. 2B). At this point, it was concluded that methylation data derived from nCATS is comparable to data derived from pyrosequencing assays when applied to a homogeneous sample (e.g. an immortalized glioma cell line).

Figure 2C:
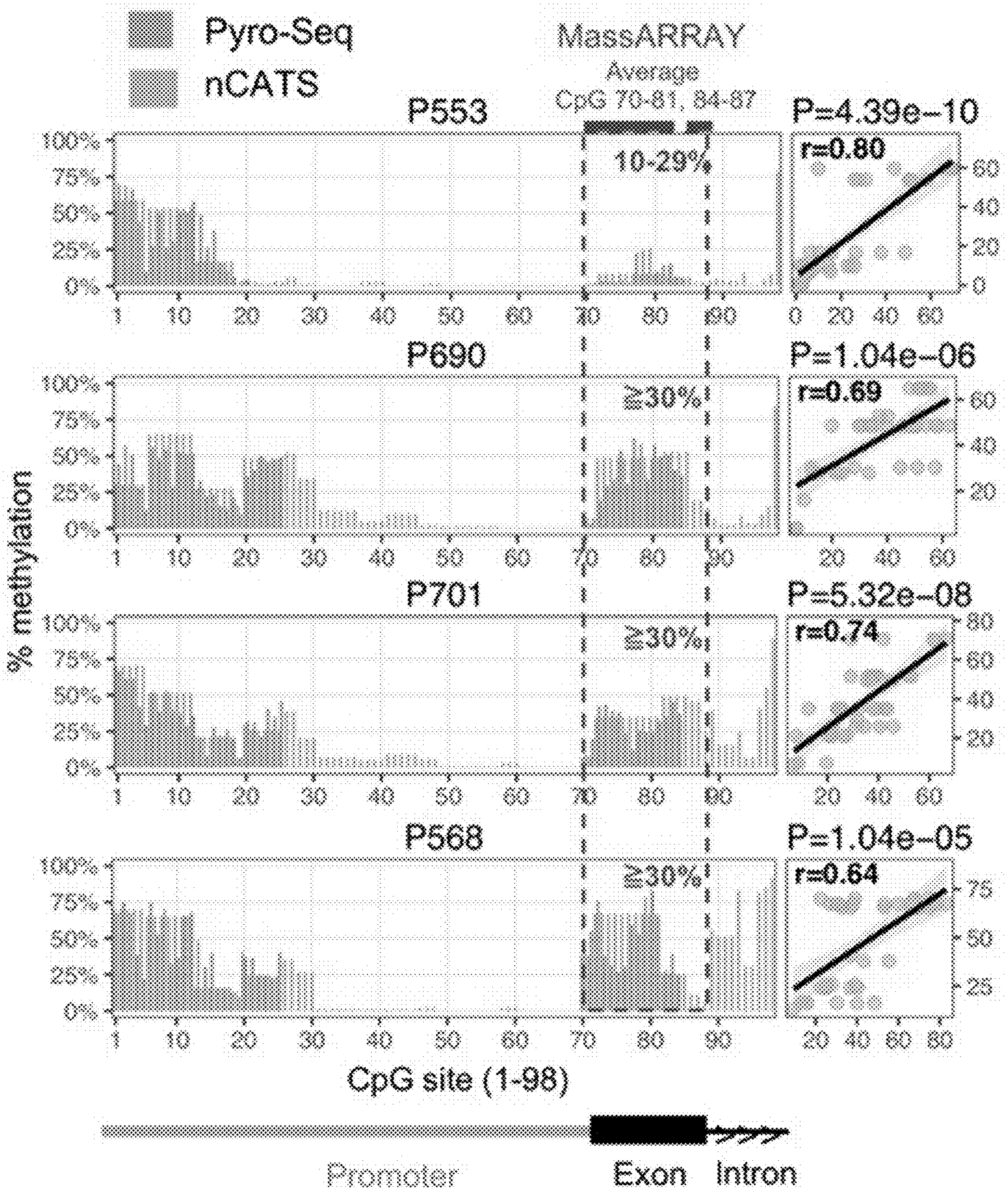

(iii) Simultaneous Evaluation of Methylation and Mutation Biomarkers in Patients with Diffuse Glioma Next, it was confirmed that nCATS can be used in clinical samples that have heterogenous cell populations opposed to the glioma cell lines. To test the accuracy of nCATS to assay MGMT methylation and IDH1/2 mutations in clinical samples. For MGMT methylation, the nCATS data was compared to data generated with bisulfite modification-PCR-pyrosequencing or the MassARRAY® System performed by 2 independent Clinical Laboratory Improvement Amendments (CLIA)-certified labs. There was a statistically significant positive correlation ($r=0\ 0.64$, $P=1.04\times10^{-5}$ to $r=0.80$, $P=4.39\times10^{-10}$) between nCATS quantitative methylation and pyrosequencing (FIG. 2C). MassARRAY® results were semiquantitative and only denoted methylation levels in 3 categories (not detected: <10%; low methylation: 10-30%; detected: >30%) for CpG sites 70-81 and 84-87. These MassARRAY® results also showed a similar trend with nCATS results over the same CpG sites.

The sample from patient 553 had 8% methylation over the targeted CpG sites, and MassARRAY® determined it to have a low level of methylation. In the other 3 patients, methylation ranged from 38% to 51%, and MassARRAY® reported "detected" methylation (i.e., >30%) (FIG. 2C). It is worth noting that fresh biopsies were used for nCATS and pyrosequencing, while formalin-fixed, paraffin-embedded samples were used in the MassARRAY® System.

Figure 2D:
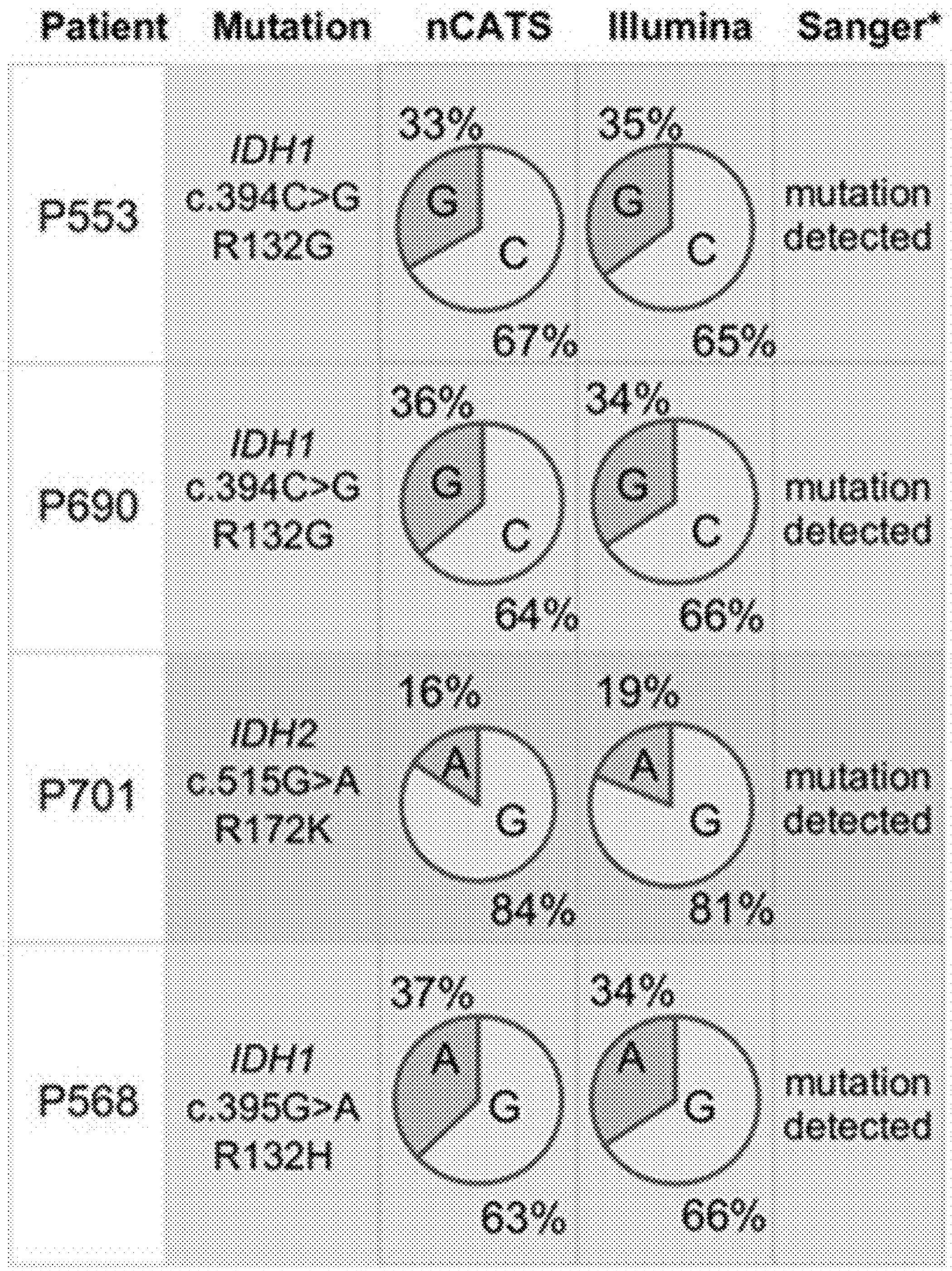

With respect to detecting IDH mutations, nCATS showed IDH mutations in all patient samples consistent with Sanger (CLIA-certified lab) and exome sequencing (Illumina) data. The allele frequencies detected by nCATS and Illumina were similar (within ±3%), P=0.91892 (chi-squared test) (FIG. 2D).

Figure 3A:
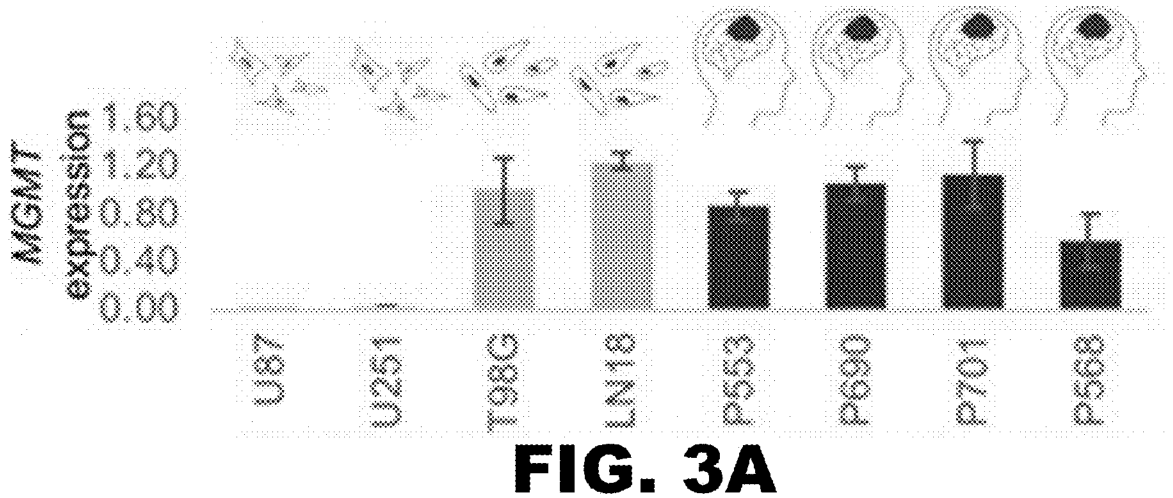
FIG. 3A-3E show correlation between MGMT gene expression and CpG methylation at different loci.
Figure 3B:
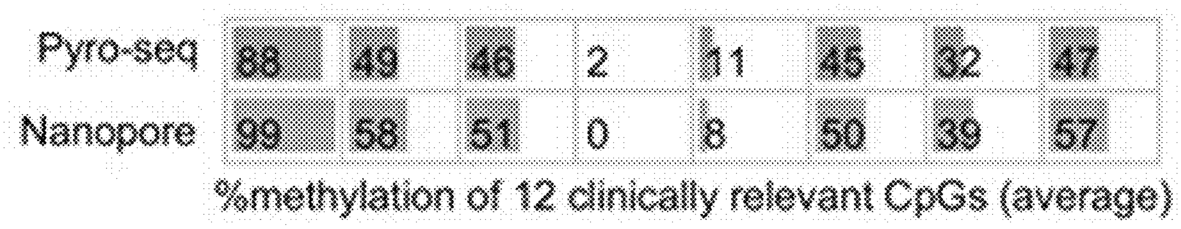
Figure 3C:
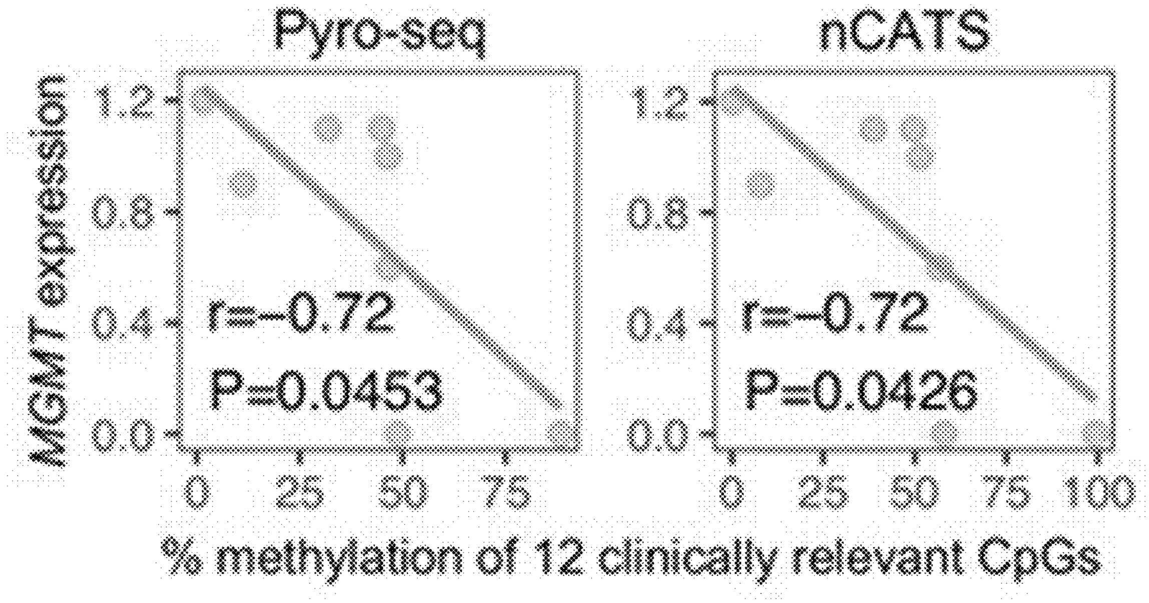

(iv) MGMT Expression Negatively Correlates with MGMT Exon Methylation but Positively Correlates with MGMT Intron Methylation Next, the relationship between MGMT gene expression and MGMT methylation level in the 4 cell lines and 4 tumor samples were determined. MGMT expression negatively correlates to TMZ clinical response. A total of 12 CpGs in differentially methylated region 2 (DMR2, in this study CpGs 70-81 in exon 1) were considered because not only could we compare nCATS and pyrosequencing data, but these CpGs are clinically relevant. As expected, qRT-PCR demonstrated high MGMT expression in TMZ-resistant cell lines and very low MGMT expression in TMZ-sensitive cell lines (FIG. 3A). An inverse correlation between MGMT expression and methylation (FIG. 3B) was shown with both nCATS and pyrosequencing ($r=-0.72$), with similar significance levels ($P<0.05$) (FIG. 3C). These data suggested that in general nCATS produced sequencing data comparable to that of conventional methods.

Figure 3D:
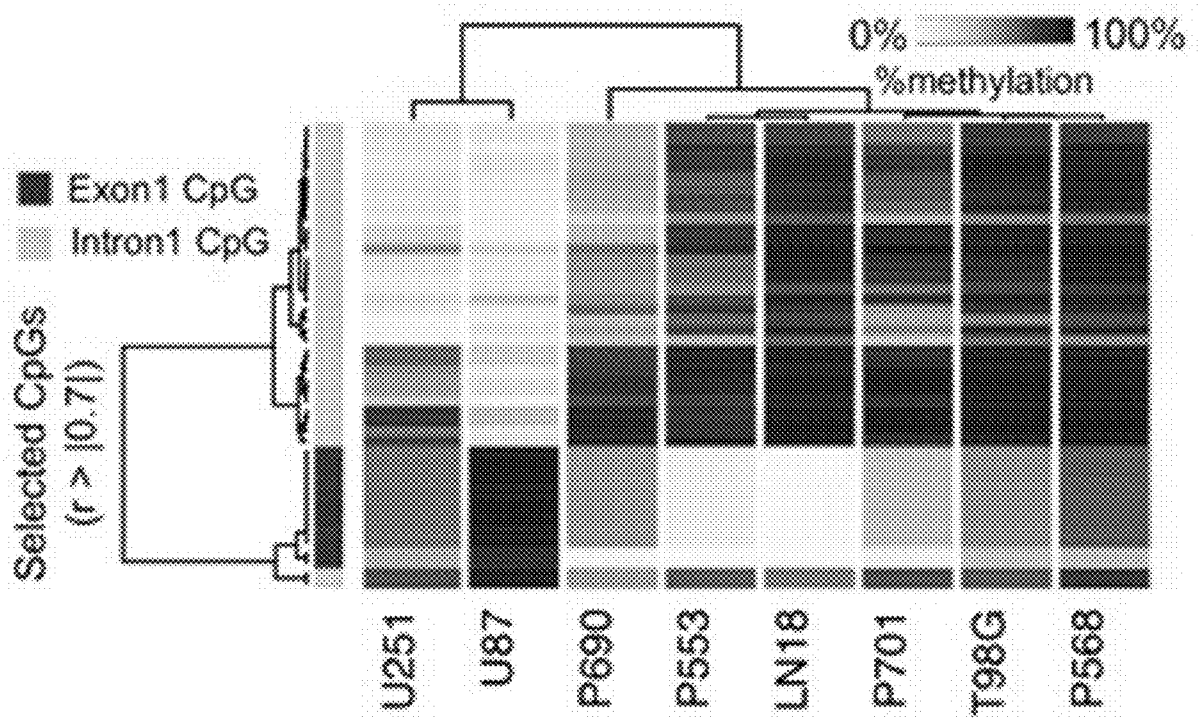
Figure 3E:
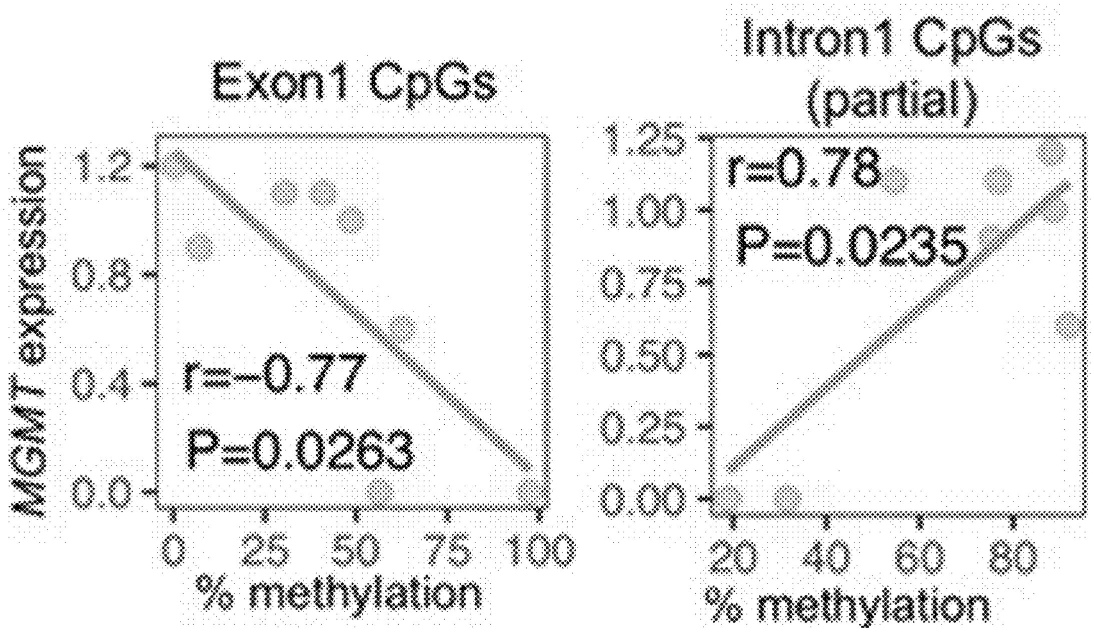

Each sample was further investigated in detail which resulted in the identification of an unexpected result in the T98G cell line. Although, high expression of MGMT was observed as previous studies [Moen E L, et al., (2014) Mol Cancer Ther 13:1334-1344] the observed methylation level and gene expression were not opposed (FIG. 3A and FIG. 3B). This unexpected result led to the investigation of the methylation of additional CpGs with nCATS (CpG 99-219). CpGs that had strong correlation ($r>0.7$ or $r<-0.7$) between MGMT expression and methylation were selected for by clustering analysis including 12 CpGs in the exon 1 and 34 CpGs in the intron 1. Hierarchical clustering according to CpG sites showed 2 clear position-dependent clusters: CpGs in exon 1 were clustered together and separated from CpGs in intron 1 (FIG. 3D). Hierarchical clustering of the 8 samples (4 cell lines and 4 tumors) demonstrated 2 distinct clusters: 2 TMZ-sensitive cell lines with similar methylation profiles were clustered together, while 2 TMZ-resistant cell lines and the 4 clinical samples were clustered together (FIG. 3D). Moreover, it was found that intronic CpG methylation positively correlated with MGMT expression (r=0.78, P=0.024); whereas, exonic CpG methylation remained negatively correlated with MGMT expression (r=−0.77, P=0.026) (FIG. 3E).

Figure 4A:
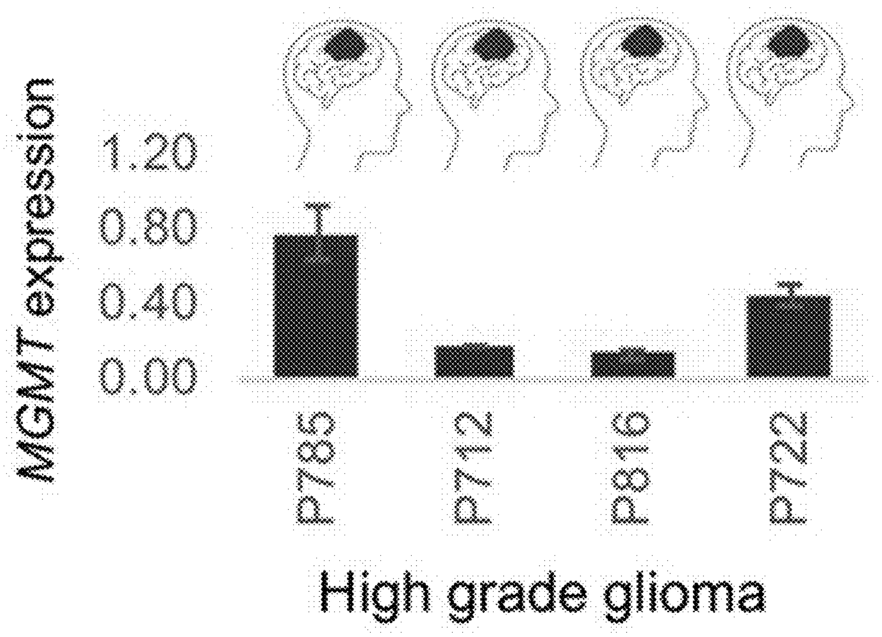
FIG. 4A-4D show nCATS can simultaneously quantify MGMT CpG methylation and detect Single nucleotide variants (SNVs) in glioma clinical samples.
Figure 4B:
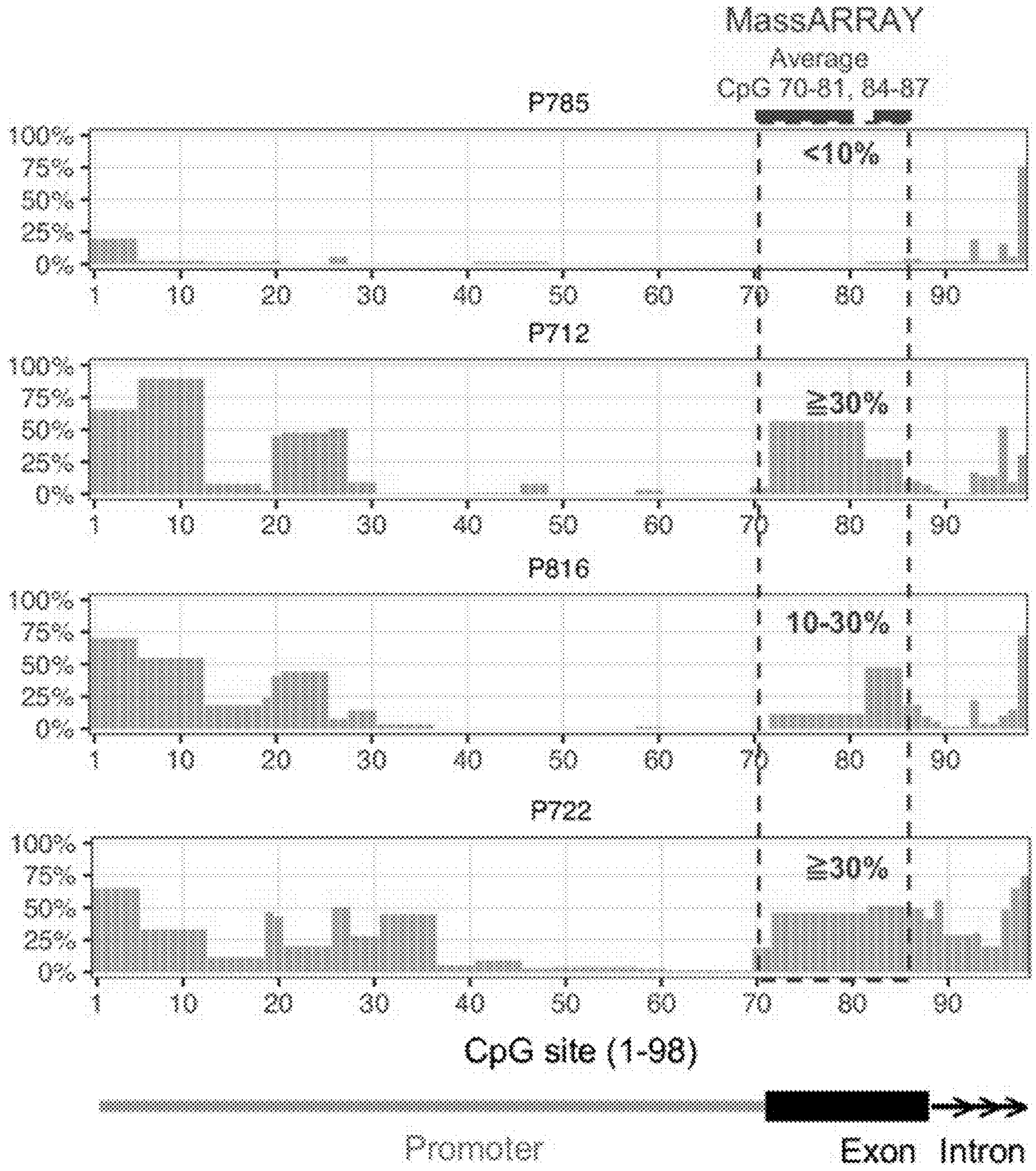
Figure 4C:
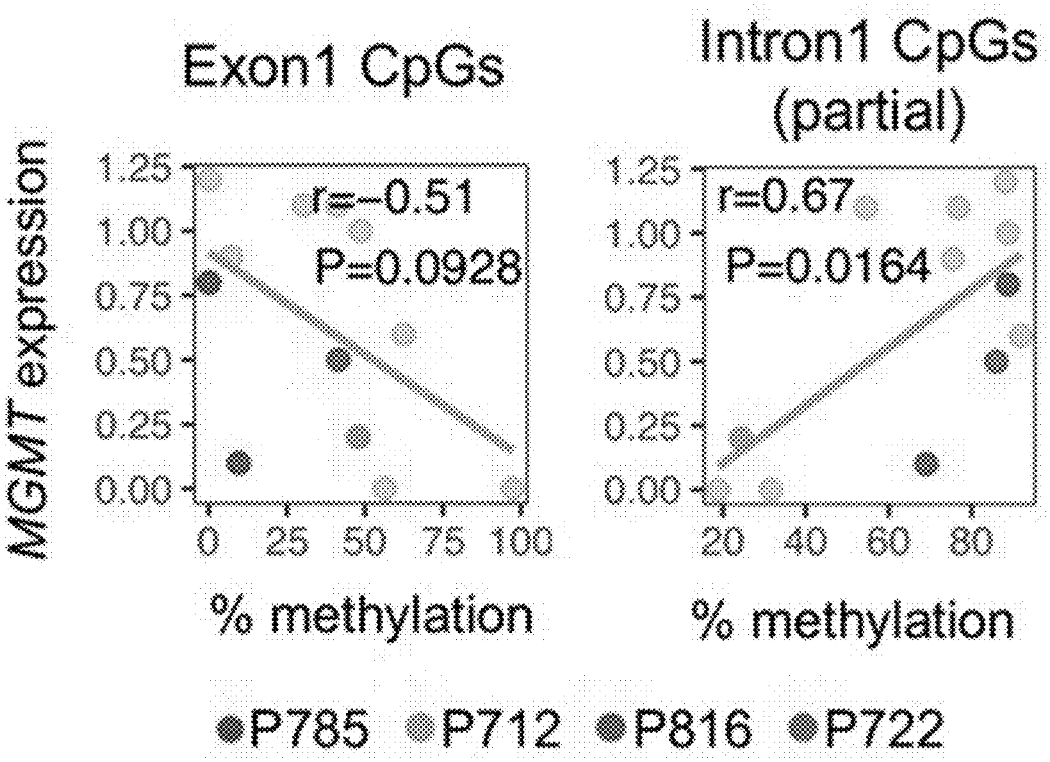

To test additional tumor grades, 4 tumor samples classified as primary WHO grade Ill or IV (high-grade gliomas) were assayed with qRT-PCR for MGMT expression and nCATS for methylation. These 4 samples differed from the previous clinical samples not only in tumor classification, but they came from IDH wild type patients. MGMT expression (FIG. 4A) and MGMT methylation pattern (FIG. 4B) varied between samples. The data for these 4 samples were combined with data for the 8 previous samples (including cell lines) for correlation analysis. With 12 samples, a negative correlation between MGMT expression and methylation in exon 1 was present (r=−0.51) but not statistically significant (P=0.093). However, there was a statistically significant positive correlation for MGMT expression and methylation in intron 1 (r=0.67, P=0.016) (FIG. 4C). For IDH genotyping in these last four clinical samples, nCATS detected IDH1 and IDH2 as wild type, consistent with Illumina™ and Sanger sequencing results.

(v) nCATS Identified Single Nucleotide Variants

Figure 4D:
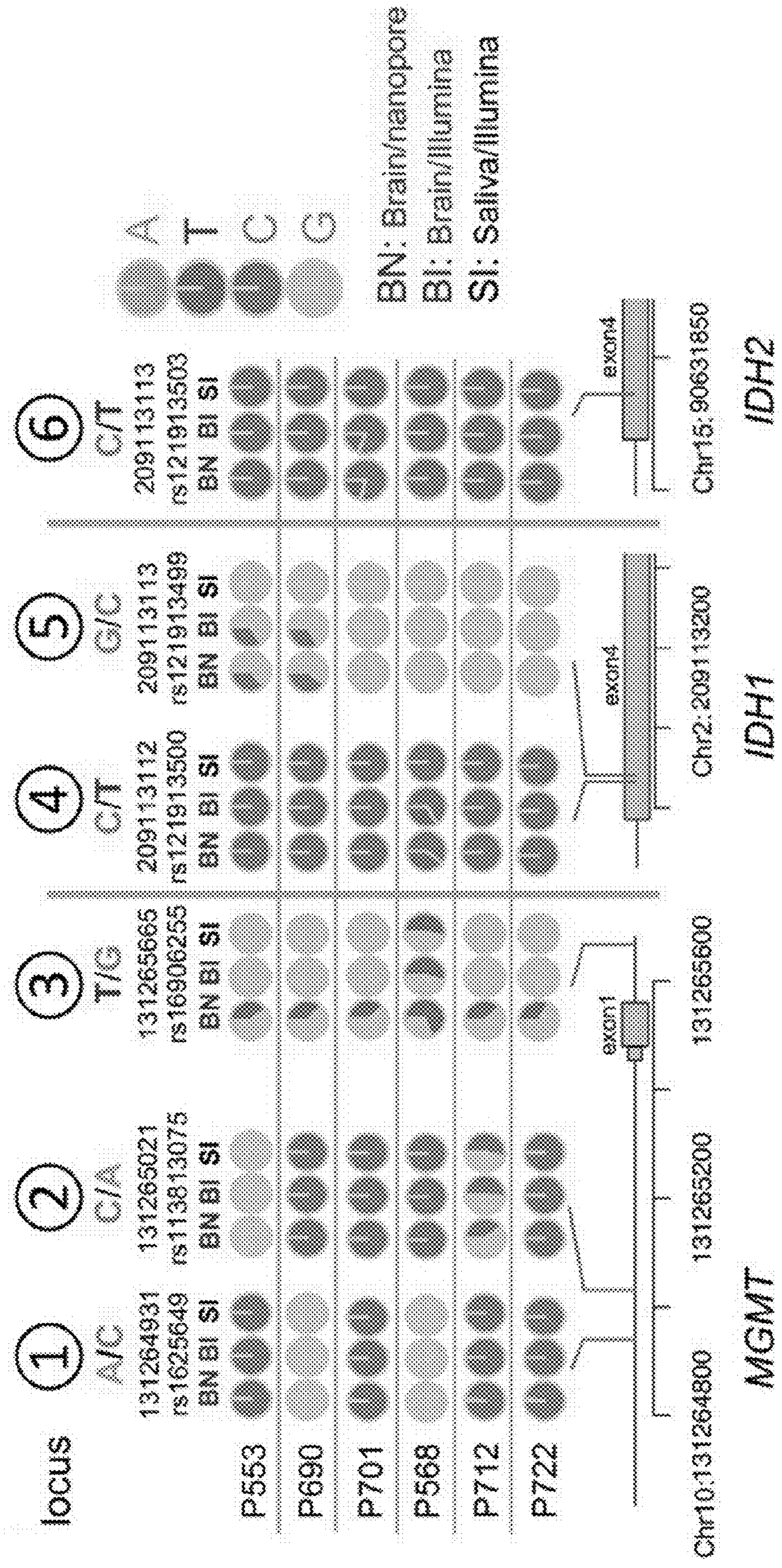

Finally, it was shown that nCATS could be used to identify single nucleotide variants (SNVs) in MGMT and IDH1/2 loci (FIG. 4D). Nanopore sequencing was compared with Illumina™ sequencing and also verified the absence of the pathogenic SNVs in germ-cell DNA using Illumina™-sequenced saliva samples from 6 of the patients (no Illumina™ data available for P785 and P816). nCATS and Illumina™ returned similar genotypes for MGMT loci 1 and 2 (FIG. 4D). For locus 2, both methods detected heterozygous alleles (C/A) in both tumor and saliva from Patient 712. For locus 3, nCATS detected heterozygous alleles in all samples, while Illumina™ showed heterozygous alleles in only 1 sample. For loci 4, 5 (IDH1), and 6 (IDH2), nCATS and Illumina™ consistently detected somatic variants (the variants were not identified in saliva samples).

DISCUSSION

In this Example, nanopore Cas9-targeted long-read sequencing (nCATS) was used to simultaneously assess 2 prognostic molecular markers in diffuse glioma clinical samples and cell lines—MGMT methylation and IDH1/2 mutations. nCATS enables enrichment of genomic regions without amplification, quantitative analysis of methylation on native DNA, and identification of single nucleotide variants. Gilpatrick et al. assessed clinical cancer biomarkers (e.g., TP53, KRAS, and BRAF) with nCATS in breast cancer cell lines and 1 patient tumor sample, demonstrating its feasibility [Gilpatrick T, et al (2020) Nat Biotechnol: 1-6]. Here, it was demonstrated the feasibility of using nCATS on several clinical solid tumor samples to assess both genetic and epigenetic prognostic biomarkers that are clinically relevant.

nCATS allowed for simultaneous evaluation of IDH1/2 mutational status and MGMT methylation level in a streamlined workflow, resulting in biomarker assessment within 36 h (FIG. 1C). The ability of nanopore sequencing to evaluate methylation from native DNA sequences obviated the need for bisulfite modification, and the present Example was were able to achieve adequate depth coverage without amplification even in clinical samples. The assessment of IDH mutational status correlated with clinically used Sanger methods and was further compared with Illumina™ sequencing (FIG. 4D).

MGMT methylation assessment is currently highly variable, as both the methodology used and the gene region evaluated are not consistent between clinicians. Further, no cutoff value in MGMT methylation level has been verified to correlate with MGMT expression; thus, no clinical consensus exists [Mansouri A, et al (2018) Neuro Oncol; Christians A, et al (2012) PLoS One 7:e33449]. Many institutions evaluate 2 differentially methylated regions (DMRs) within the MGMT promoter and exon 1 that have been shown to correlate with MGMT expression in cell lines and patient cohorts; MGMT methylation is then used to predict responsiveness to temozolomide (TMZ) therapy. Our institution uses MassARRAY® and stratifies patients into 3 groups: no methylation (<10%), low methylation (10-30%), and high methylation (>30%). In this study, nCATS data from both cell lines and patient samples correlated with both MassARRAY® data and pyrosequencing (FIG. 2C and FIG. 4B). However, some patients who are below this arbitrary cutoff value (e.g., 10%) do respond to TMZ therapy [Dovek L, et al (2019). Neuro-Oncology Pract. 6(3):194-202; Johannessen L E, et al. (2018) Cancer Genomics Proteomics 15:437-446; and Radke J, et al (2019) Acta Neuropathol Commun 7:89], placing them in a "gray zone" and producing a clinical quandary. With this in mind, Chai et al. developed a novel CpG averaging model for pyrosequencing data that defines the MGMT promoter as being methylated when at least 3 CpGs exceed their respective cutoff values; this allows clinicians to better stratify patients with very low levels of methylation (e.g., <10%) [Chai R-C, et al (2019) Mod Pathol 32:4-15]. We demonstrate that nCATS can be used to quantify CpG methylation in multiple regions of the MGMT gene and may provide further insight into the variability of treatment responses.

Given the long-read sequencing capacity of nCATS, we were also able to quantify CpG methylation along the entire MGMT promoter, exon 1, and a portion of intron 1. One of the TMZ-resistant cell lines (T98G) did not have the expected inverse correlation between MGMT promoter methylation level and MGMT expression. There was a positive correlation between methylation of intronic CpG sites and MGMT expression for all GBM cell lines, the IDH mutant sample, and wild type DG samples (FIG. 3E and FIG. 4C). This finding suggests a potential benefit of assaying gene body methylation, as the intron could be important for determining MGMT expression.

Finally, 2 SNVs were identified in the promoter region of MGMT, and one of them (rs1625649) had prognostic impact on patients with MGMT methylated glioblastoma [Hsu C-Y et al., (2017) PLOS One 12: e0186430; and Xu M, et al., (2014) Carcinogenesis 35:564-571]. In MGMT, inconsistency between nCATS and Illumina™ result was also observed. In locus no. 3 (FIG. 4D), nCATS detected 2 alleles in all patients while Illumina™ showed 2 alleles in only P568. We then considered the DNA sequence in this region and found 6 consecutive guanines (homopolymer) in this locus. For the current version of nanopore, homopolymer rich regions are the major source of errors. Therefore, for this locus, nCATS could not deliver accurate genotyping when using this version of nanopore (R9.4.1). An updated version of nanopore is being developed that incorporates a longer sensor to overcome errors in homopolymer rich regions.

Our nCATS technique also identified mutation variants (locus no.4-5 (FIG. 4)) in IDH1 and IDH2. The variants in IDH1 are associated with survival in patients with acute myeloid leukemia, but their prognostic value in GBM is not known. However, with the advent of new IDH-directed therapies, variants in IDH1/2 may be of significance in the future. These insights could lead to the incorporation of SNVs as an additional factor in therapeutic decision making, which can be done contemporaneously along with biomarker identification with nCATS.

In conclusion, the nCATS technique provides results within 2 days of surgical resection, potentially at lower capital cost than traditional methods. The feasibility in clinical solid tumor samples was demonstrated and used DG as a model given that both genetic and epigenetic biomarkers are used clinically. The nCATS method also provided assessment of MGMT methylation throughout a larger gene region in comparison to currently used methods. There is great potential to use nCATS clinically to standardize molecular marker testing in DG and provide insights into patient variability to treatment response. Furthermore, nanopore platforms can be cost-effective and high-throughput, making them accessible in countries with limited resources. nCATs requires >3 μg of high-quality DNA as starting material, making testing formalin-fixed specimens impractical. Obtaining tissue from fresh samples requires consideration of choosing a region with low necrosis and high tumor content in order to optimize DNA extraction. Nevertheless, the nCATS method provides a promising tool for enhancing cancer precision medicine with the potential for simultaneously assessing multiple molecular targets.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All references, patents and patent applications disclosed herein are incorporated by reference with respect to the subject matter for which each is cited, which in some cases may encompass the entirety of the document.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

What is claimed is:

1. A method of treating a diffuse glioma in a human subject in need thereof, the method comprising:

a) obtaining or having obtained a biological sample from the human subject;

b) isolating genomic DNA from the sample;

c) detecting or having detected simultaneously the mutational status of IDH1 or IDH2 genes and methylation levels in MGMT gene, including 5' and 3' flanking regions of the genes; wherein:

(i) the mutational status of IDH1 comprises a substitution at R132;

(ii) the mutational status of IDH2 comprises a substitution at R172; and (iii) the methylation levels in the MGMT gene comprises methylation levels in at least a portion of exon 1 and intron 1 of the MGMT gene;

d) comparing the mutational status and the methylation levels of the genes with a reference value;

e) indicating the human subject as having a diffuse glioma when the mutational status and the methylation levels of the genes deviate from the reference value; and f) administering to the human subject identified as having diffuse glioma, a treatment comprising chemotherapy or radiation.

2. The method of claim 1, wherein isolated genomic DNA comprise free ends and the method further comprises dephosphorylating the free DNA ends with a phosphatase.

3. The method of claim 2, wherein the isolated genomic DNA is contacted with a nuclease to generate targeted double strand breaks thereby generating one or more regions of interest.

4. The method of claim 1, wherein: (i) the substitution at R132of the IDH1 gene is selected from R132H, R132S, R132C, R132G, and R132L; (ii) the substitution at R172 of the IDH2 gene is R172K; and (iii) the methylation levels in the MGMT gene further comprises methylation levels in at least a portion of the promoter region.

5. The method of claim 3, wherein the nuclease comprise a Cas9 and targeted double strand breaks are generated with crRNAs, wherein each of the crRNA for IDH1 binds specifically to a sequence in IDH1 gene; each of the crRNA for IDH2 binds specifically to a sequence in IDH2 gene; and each of the crRNA for MGMT specifically binds to a sequence in MGMT gene, respectively.

6. The method of claim 5, wherein the crRNAs for MGMT comprise SEQ ID NOs: 1-2, the crRNAs for IDH1 comprise SEQ ID NOs: 3-4, and the crRNAs for IDH2 comprise SEQ ID NOs: 5-6.

7. The method of claim 5, further comprising modifying the free ends of the regions of interest generated by the nuclease for ligation of sequencing adaptors.

8. The method of claim 7, comprising ligating one or more sequencing adaptor molecules to the one or more regions of interest and sequencing the regions of interest.

9. The method of claim 8, wherein nanopore sequencing is used.

10. A method of treating a human subject having a diffuse glioma, the method comprising:

a) obtaining or having obtained a biological sample from the human subject;

b) isolating genomic DNA from the sample;

c) detecting or having detected methylation levels in MGMT gene, including 5' and 3' flanking regions of the gene; wherein:

the methylation levels in the MGMT gene comprises methylation levels in at least a portion of exon 1 and intron 1 of the MGMT gene;

d) comparing the methylation levels with a reference value;

e) assessing therapy responsiveness in the human subject based on the methylation level of the MGMT gene; wherein, an increase in methylation levels in at least a portion of the exon 1 of the MGMT gene; or a decrease in the methylation level in at least a portion of intron 1 of the MGMT gene indicates that the subject has a diffuse glioma that is likely to respond to a chemotherapy comprising temozolomide; and f) administering temozolomide to the human subject indicated as likely to respond to chemotherapy comprising temozolomide.

11. The method of claim 10, wherein the isolated genomic DNA comprise free ends and the method further comprises dephosphorylating the free DNA ends with a phosphatase.

12. The method of claim 11, wherein the isolated genomic DNA is contacted with a nuclease to generate targeted double strand breaks thereby generating one or more regions of interest.

13. The method of claim 10, wherein: the methylation levels in the MGMT gene further comprises methylation levels in at least a portion of the promoter region; wherein an increase in methylation levels in at least a portion the promoter indicates that the subject is likely to respond to temozolomide.

14. The method of claim 12, wherein the nuclease comprises a Cas9 and targeted double strand breaks are generated with crRNAs, wherein each of the crRNA specifically binds to a sequence in the MGMT gene.

15. The method of claim 14, wherein the crRNAs for MGMT comprise SEQ ID NOs: 1-2.

16. The method of claim 14, further comprising modifying the free ends of the regions of interest generated by the nuclease for ligation of sequencing adaptors.

17. The method of claim 16, comprising ligating one or more sequencing adaptor molecules to the regions of interest and sequencing the regions of interest.

18. The method of claim 17, wherein nanopore sequencing is used.

19. A method of treating a diffuse glioma in a human subject in need thereof, comprising: administering to the human subject a treatment comprising chemotherapy or radiation, wherein the human subject has been determined as having the diffuse glioma when mutational status of IDH1 gene or IDH2 gene and methylation levels in MGMT gene, deviate from a reference value, in a sample obtained from the human subject; and wherein, (a) the mutational status of IDH1 comprises a substitution at R132;

(b) the mutational status of IDH2 comprises a substitution at R172; and (c) the methylation levels in the MGMT gene comprises methylation levels in at least a portion of exon 1 and intron 1 of the MGMT gene.

20. A method of treating a diffuse glioma in a human subject in need thereof, comprising: administering to the human subject a treatment, wherein the human subject has been assessed as having a diffuse glioma that is likely to respond to a chemotherapy comprising temozolomide by having determined methylation levels in MGMT gene, including 5' and 3' flanking regions of the gene in a sample obtained from the human subject; wherein:

determining the methylation levels in the MGMT gene comprises determining methylation levels in at least a portion of exon 1 and intron 1 of the MGMT gene; and wherein an increase in methylation levels in at least a portion the exon 1; or a decrease in the methylation level in at least a portion of the intron 1; indicates that the human subject is likely to respond to chemotherapy comprising temozolomide.

21. The method of claim 19, wherein the methylation levels in the MGMT gene further comprises methylation levels in at least a portion of the promoter region.

22. The method of claim 20, wherein the methylation levels in MGMT gene further comprises methylation in at least a portion of the promoter and wherein an increase in methylation levels in at least a portion the promoter indicates that the subject is likely to respond to chemotherapy comprising temozolomide.

* * * * *